US011115265B2

(12) United States Patent
Shen et al.

(10) Patent No.: US 11,115,265 B2
(45) Date of Patent: Sep. 7, 2021

(54) METHOD OF WIRELESS DISCOVERY AND NETWORKING OF MEDICAL DEVICES IN CARE ENVIRONMENTS

(71) Applicant: Stryker Corporation, Kalamazoo, MI (US)

(72) Inventors: John T. Shen, San Jose, CA (US); Benjamin H. Feingold, Tucson, AZ (US); David B. Bennett, Newbury Park, CA (US); Rohitkumar Godhani, San Jose, CA (US); Mithun Gundi, San Jose, CA (US); Robert L. Jones, III, South Bend, IN (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 16/247,165

(22) Filed: Jan. 14, 2019

(65) Prior Publication Data

US 2019/0149409 A1 May 16, 2019

Related U.S. Application Data

(62) Division of application No. 15/154,406, filed on May 13, 2016, now Pat. No. 10,200,241.
(Continued)

(51) Int. Cl.
*H04L 12/24* (2006.01)
*H04L 29/08* (2006.01)
(Continued)

(52) U.S. Cl.
CPC ......... *H04L 41/0806* (2013.01); *H04L 67/12* (2013.01); *H04W 4/08* (2013.01);
(Continued)

(58) Field of Classification Search
CPC .... H04L 41/0806; H04L 67/12; H04W 84/20; H04W 80/00; H04W 8/005; H04W 88/16
See application file for complete search history.

(56) References Cited

U.S. PATENT DOCUMENTS 4,703,359 A 10/1987 Rumbolt et al.
4,756,007 A 7/1988 Qureshi et al.
(Continued)

FOREIGN PATENT DOCUMENTS

EP 1 061 451 A2 12/2000
EP 1 432 151 A1 6/2004
(Continued)

OTHER PUBLICATIONS

U.S. Non-Final Office Action dated Apr. 18, 2018, for U.S. Appl. No. 15/154,406, filed May 13, 2016, 15 pages.
(Continued)

*Primary Examiner* — Deepa Belur
(74) *Attorney, Agent, or Firm* — Morrison & Foerster LLP

(57) ABSTRACT

A system for automatically establishing a network. The system includes a main device group including a main wireless transceiver device, a control device and a first network interface and a secondary device group including a secondary wireless transceiver device, a secondary device group slave device and a second network interface. The main wireless transceiver device wirelessly communicating with the secondary wireless transceiver device to instruct the main device group and the secondary device group to form a network wherein the control device communicates with the secondary device group slave device over the first network interface and the second network interface, respectively. The control device wirelessly controls functions of the secondary device group slave device with instructions sent over the network. The main wireless transceiver device only wire-
(Continued)

lessly communicates with the secondary wireless transceiver device when the main wireless transceiver device and the secondary wireless transceiver device are in a location.

43 Claims, 14 Drawing Sheets

Related U.S. Application Data

(60) Provisional application No. 62/160,935, filed on May 13, 2015.

(51) Int. Cl.
| | |
|---|---|
| *H04W 8/00* | (2009.01) |
| *H04W 4/08* | (2009.01) |
| *H04W 4/30* | (2018.01) |
| *H04W 84/20* | (2009.01) |
| *H04W 88/16* | (2009.01) |
| *H04W 84/12* | (2009.01) |
| *H04W 80/00* | (2009.01) |

(52) U.S. Cl.
CPC ............. *H04W 4/30* (2018.02); *H04W 8/005* (2013.01); *H04W 80/00* (2013.01); *H04W 84/12* (2013.01); *H04W 84/20* (2013.01); *H04W 88/16* (2013.01)

(56) References Cited

U.S. PATENT DOCUMENTS

| | | | |
|---|---|---|---|
| 4,780,883 A | 10/1988 | O'Connor et al. | |
| 4,796,025 A | 1/1989 | Farley et al. | |
| 5,008,902 A | 4/1991 | Key et al. | |
| 5,319,363 A | 6/1994 | Welch et al. | |
| 5,609,560 A | 3/1997 | Ichikawa et al. | |
| 5,740,801 A | 4/1998 | Branson | |
| 5,877,819 A | 3/1999 | Branson | |
| 6,115,384 A | 9/2000 | Parzych | |
| 6,397,259 B1 | 5/2002 | Lincke et al. | |
| 6,581,117 B1 | 6/2003 | Klein et al. | |
| 6,704,293 B1 | 3/2004 | Larsson et al. | |
| 6,928,490 B1 | 8/2005 | Bucholz et al. | |
| 7,103,578 B2 | 9/2006 | Beck et al. | |
| 7,242,306 B2 | 7/2007 | Wildman et al. | |
| 7,366,934 B1 | 4/2008 | Narayan et al. | |
| 7,660,420 B1 | 2/2010 | Narayan et al. | |
| 7,814,516 B2 | 10/2010 | Stecyk et al. | |
| 7,844,657 B2 | 11/2010 | Novak | |
| 8,175,590 B2 | 5/2012 | Hamel et al. | |
| 9,902,495 B2 | 2/2018 | Phan et al. | |
| 10,200,241 B2 | 2/2019 | Shen | |
| 10,492,102 B2* | 11/2019 | Raleigh ................... H04L 69/18 | |
| 2002/0161317 A1 | 10/2002 | Risk et al. | |
| 2003/0025604 A1 | 2/2003 | Freeman | |
| 2003/0093503 A1 | 5/2003 | Yamaki et al. | |
| 2003/0123624 A1 | 7/2003 | Colemon | |
| 2003/0142683 A1 | 7/2003 | Lam et al. | |
| 2005/0035862 A1 | 2/2005 | Wildman et al. | |
| 2005/0080403 A1 | 4/2005 | Takahashi | |
| 2005/0251228 A1 | 11/2005 | Hamel | |
| 2006/0116667 A1 | 6/2006 | Hamel et al. | |
| 2006/0165371 A1 | 7/2006 | Zwart | |
| 2007/0107068 A1 | 5/2007 | Kelley et al. | |
| 2007/0135866 A1 | 6/2007 | Baker et al. | |
| 2007/0161904 A1 | 7/2007 | Urbano | |
| 2008/0089277 A1* | 4/2008 | Alexander ............ H04W 8/005 370/328 |
| 2008/0137646 A1 | 6/2008 | Agarwal et al. | |
| 2008/0140158 A1 | 6/2008 | Hamel et al. | |
| 2008/0281165 A1* | 11/2008 | Rai ....................... H04L 67/125 600/300 |
| 2008/0303707 A1 | 12/2008 | Larsen et al. | |
| 2009/0080348 A1 | 3/2009 | Hamel et al. | |
| 2009/0121865 A1 | 5/2009 | Hamel et al. | |
| 2010/0146053 A1 | 6/2010 | Jiang | |
| 2010/0177703 A1* | 7/2010 | daCosta .................. H04L 41/12 370/328 |
| 2012/0226771 A1 | 9/2012 | Harrington et al. | |
| 2012/0274586 A1 | 11/2012 | Southworth et al. | |
| 2012/0287932 A1 | 11/2012 | Haddad et al. | |
| 2013/0198291 A1 | 8/2013 | Wang | |
| 2013/0267779 A1 | 10/2013 | Woolford et al. | |
| 2013/0275574 A1 | 10/2013 | Hugard, IV et al. | |
| 2013/0294285 A1* | 11/2013 | Zhang ................... H04W 24/02 370/254 |
| 2014/0269255 A1* | 9/2014 | Zeng ..................... H04W 24/04 370/219 |
| 2015/0029880 A1* | 1/2015 | Burns ..................... G01S 11/16 370/252 |
| 2015/0245290 A1* | 8/2015 | Liu ................... H04W 52/0216 370/311 |
| 2015/0256385 A1* | 9/2015 | Chandhok ............... H04L 41/18 715/734 |
| 2016/0036540 A1* | 2/2016 | Fang ..................... H04W 24/08 370/252 |
| 2016/0117813 A1* | 4/2016 | Gross .................... G16H 40/60 600/474 |
| 2016/0151544 A1 | 6/2016 | Nakano | |
| 2016/0315982 A1* | 10/2016 | Wallace ............... H04L 41/0816 |
| 2016/0316030 A1 | 10/2016 | Wei et al. | |
| 2017/0156103 A1* | 6/2017 | Auvray ................. H04W 48/08 |
| 2017/0208528 A1 | 7/2017 | Zhang et al. | |
| 2017/0366368 A1 | 12/2017 | Crayford et al. | |
| 2018/0011932 A1 | 1/2018 | Gerst et al. | |
| 2018/0317067 A1* | 11/2018 | Ameixieira ........... H04W 76/10 |
| 2019/0162471 A1 | 5/2019 | Stewart | |
| 2019/0327782 A1* | 10/2019 | Yang .................... H04W 76/16 |

FOREIGN PATENT DOCUMENTS

| | | | |
|---|---|---|---|
| EP | 1 681 031 A1 | 7/2006 | |
| EP | 2993955 A1 * | 3/2016 | ............ H04W 84/20 |
| JP | 06-114065 A | 4/1994 | |
| WO | WO 01/89362 A2 | 11/2001 | |
| WO | WO 02/100262 A1 | 12/2002 | |
| WO | WO 2009/151535 A1 | 12/2009 | |

OTHER PUBLICATIONS

U.S. Notice of Allowance dated Sep. 19, 2018, for U.S. Appl. No. 15/154,406, filed May 13, 2016, 14 pages.
U.S. Restriction Requirement dated Dec. 13, 2017, for U.S. Appl. No. 15/154,406, filed May 13, 2016, 5 pages.

* cited by examiner

METHOD OF WIRELESS DISCOVERY AND NETWORKING OF MEDICAL DEVICES IN CARE ENVIRONMENTS

CROSS REFERENCE TO RELATED APPLICATIONS

This is a divisional of U.S. application Ser. No. 15/154,406, filed May 13, 2016, which claims the benefit of U.S. Provisional Application Ser. No. 62/160,935, filed May 13, 2015.

FIELD OF THE INVENTION

The present invention relates to a method of configuring devices in an operating theater.

BACKGROUND OF THE INVENTION

Surgeons use many devices to help them during operative procedures. Currently, surgeons or other people in the operative theater have had to connect all cooperating devices by wiring the devices together or actively setting up a wireless network for each device in the operative theater before surgery. An easier method of networking devices in an operative theater is desired.

SUMMARY OF THE INVENTION

The present invention, according to one aspect, is directed to a system for automatically establishing a network. The system has a main device group including a main wireless transceiver device, a control device and a first network interface. The system also has a secondary device group including a secondary wireless transceiver device, a secondary device group slave device and a second network interface. The secondary device group is spaced from the main device group. The main wireless transceiver device wirelessly communicates with the secondary wireless transceiver device to instruct the main device group and the secondary device group to form a network wherein the control device communicates with the secondary device group slave device over the first network interface and the second network interface, respectively. The control device wirelessly controls functions of the secondary device group slave device with instructions sent over the network. The main wireless transceiver device only wirelessly communicates with the secondary wireless transceiver device when the main wireless transceiver device and the secondary wireless transceiver device are in a single location. Wireless communications of the main wireless transceiver device and the secondary wireless transceiver device are not able to pass through walls of the single location.

Another aspect of the present invention is to provide a method for controlling a device. The method includes providing a main device group including a main wireless transceiver device, a control device and a first network interface. The method also includes providing a secondary device group including a secondary wireless transceiver device, a slave device and a second network interface. The method further includes spacing the secondary device group from the main device group, wirelessly communicating network information from the main wireless transceiver device to the secondary wireless transceiver device, forming a network over the first network interface and the second network interface using the network information, and controlling functions of the slave device with the control device through instructions sent over the network. The step of wirelessly communicating network information only occurs when the main wireless transceiver device and the secondary wireless transceiver device are in a single location. Wireless communications of the main wireless transceiver device and the secondary wireless transceiver device are not able to pass through walls of the single location.

BRIEF DESCRIPTION OF THE DRAWINGS

One or more embodiments of the present invention are illustrated by way of example and should not be construed as being limited to the specific embodiments depicted in the accompanying drawings, in which like reference numerals indicate similar elements.

Figure 1A:
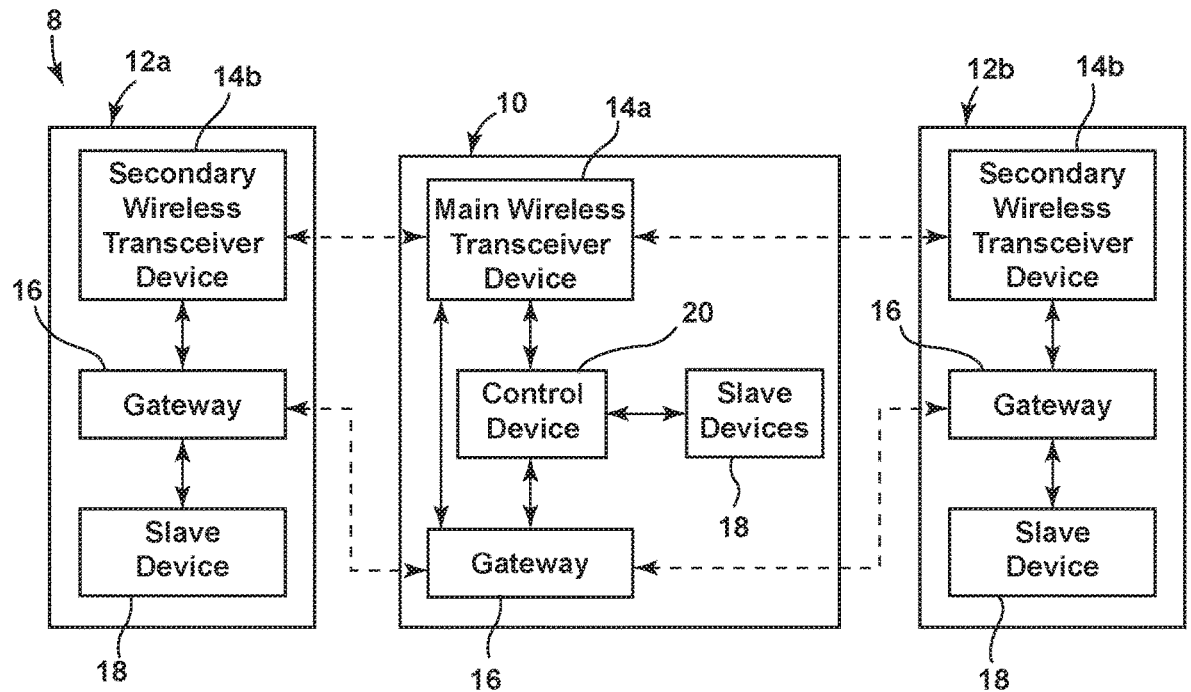
FIG. 1A is a schematic view of a system for automatically networking devices in an operating room embodying an aspect of the present invention.

The specific devices and processes illustrated in the attached drawings, and described in the following specification are simply exemplary embodiments of the inventive concepts. Hence, specific dimensions and other physical characteristics relating to the embodiments disclosed herein are not to be considered as limiting.

DETAILED DESCRIPTION

For purposes of description herein, it is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The reference number 8 (FIG. 1A) generally designates a schematic of a system for automatically networking devices in an operating room 100 (see FIG. 7) embodying an aspect of the present invention. The system 8 includes a plurality of device groups including a main device group 10 and at least one secondary device group 12a, 12b. Each of the device groups 10, 12a, 12b can be located on a portable cart 99 (see FIG. 7) or can be stationary within a room (e.g., on fixed shelving). The main device group 10 includes a control device 20 that is configured to control slave devices 18 in the main device group 10 and in the secondary device groups 12a, 12b. The system 8 for automatically networking devices automatically establishes a wireless network including the control device 20 and the slave devices 18 to allow the control device 20 to control the slave devices 18 in the at least one secondary device group 12a, 12b. The system 8 for automatically networking devices employs a main wireless transceiver device 14a and at least one secondary wireless transceiver device 14b to establish the wireless network including the control device 20 and the slave devices 18.

The illustrated main device group 10 includes the control device 20. The secondary device groups 12a, 12b can include a secondary control device 20. While only two secondary device groups 12a, 12b are shown, any number of secondary device groups 12a, 12b could be used (including only one secondary device group). Two secondary device groups 12a, 12b are illustrated in FIG. 1A to show that multiple secondary device groups 12a, 12b can be used in the system 8 for automatically networking devices.

In the illustrated example, the main device group 10 as illustrated in FIG. 1A includes the control device 20, at least one of the slave devices 18, the main wireless transceiver device 14a and a network interface or gateway 16. As discussed in more detail below, the control device 20 includes an interface for controlling the slave devices 18. The interface of the control device 20 can be used to control one slave device 18 at a time or can be used to control multiple slave devices 18 simultaneously. The control device 20 can also be used to configure and/or update the software of the slave devices 18 as outlined in more detail below. Each slave device 18 is a device used in performing a surgical operation. At least one slave device 18 in the main device group 10 is illustrated as being directly linked by a wired system (e.g., via a USB connection) to the control device 20 for control by the control device 20. However, it is contemplated that the main device group 10 can be used without a slave device 18 or that the at least one slave device 18 in the main device group 10 can be wirelessly networked with the control device 20. Moreover, as discussed in more detail below, the control device 20 and the at least one slave device 18 in the main device group 10 can be integrated into a single unit or housing.

The illustrated gateway 16 and the main wireless transceiver device 14a of the main device group 10 allow the control device 20 to be wirelessly networked with the slave devices 18 of the secondary device groups 12a, 12b. The gateway 16 allows the control device 20 to communicate wirelessly and allows for several different devices using various communication standards to communicate over a single wireless network. The gateway 16 has a plurality of inputs (e.g., USB and Ethernet) along with a wireless transceiver (e.g., Wi-Fi). Therefore, a plurality of different devices using different communication standards can be connected to a single device (i.e., the gateway 16) and can communicate with other devices in a wireless network including the control device 20. The gateway 16 can also take the form of a router for connecting to a hospital network (e.g., HIS) and/or the Internet (either using a wired connection or wirelessly). The gateway 16 also allows a device without wireless communication capabilities to communicate wirelessly when the device without wireless communication capabilities is connected thereto. The main wireless transceiver device 14a communicates with the secondary wireless transceiver devices 14b and the control device 20 to facilitate establishment of the wireless network.

In the illustrated example, the secondary wireless transceiver devices 14b are wired to the gateway 16 (e.g., via USB) to provide instructions to the gateway 16 as outlined below. Each secondary device group 12a, 12b also includes the slave devices 18 wired to the gateway 16 (e.g., via USB) for allowing the slave devices 18 to communicate wirelessly with the gateway 16 in the main device group 10, thereby allowing the control device 20 to control the slave devices 18 (through the gateway 16). The network is established by the main wireless transceiver device 14a and the gateway 16 connected thereto and is defined by all devices in the system 8 for automatically networking devices in the operating room 100 (that is, the control device 20, the slave devices 18 and the gateways 16). It is contemplated that the wireless network could occur over a pre-established hospital network.

Figure 1B:
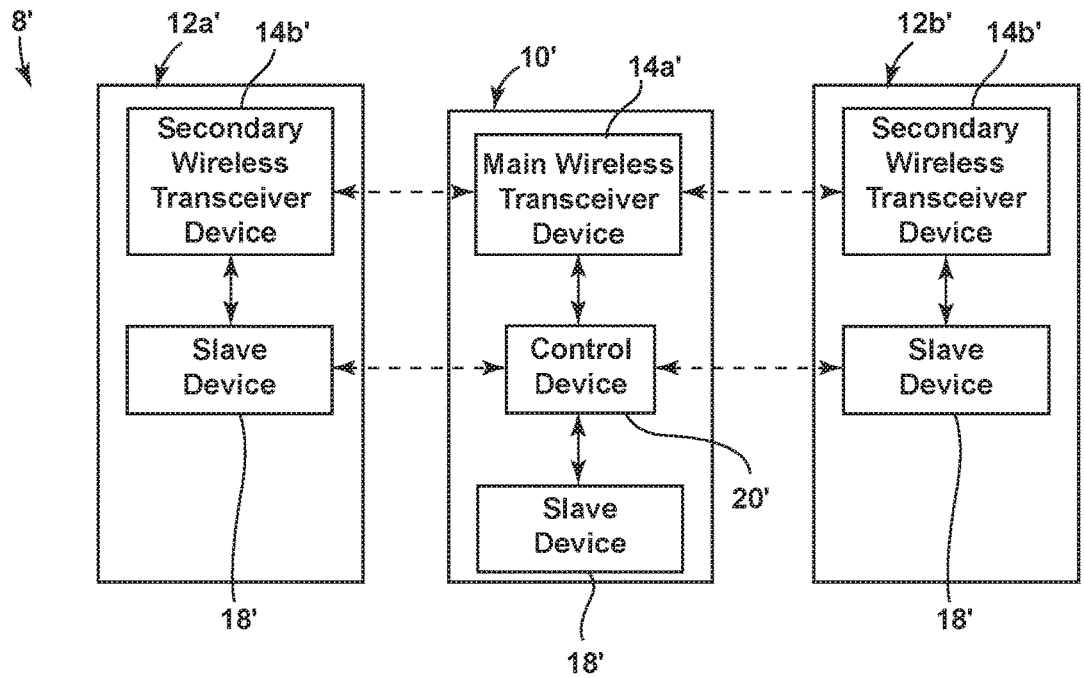
FIG. 1B is a schematic view of a system for automatically networking devices in an operating room embodying a second aspect of the present invention.

FIG. 1B illustrates a second embodiment of the system 8' for automatically networking devices. Since the system 8' for automatically networking devices is similar to the previously described system 8 for automatically networking devices, similar components appearing in FIG. 1A and FIG. 1B, respectively, are represented by the same, corresponding reference number, except for the prime suffix (') in the numerals of the latter. In the second embodiment of the system 8' for automatically networking devices, the slave devices 18' have internal wireless communication software and hardware therein, thereby obviating a need for the gateway 16 (in other words, the slave devices 18 and the gateways 16 of the first embodiment are in a single housing). It is contemplated that any secondary device group 12a, 12b with a slave device 18 that does not include wireless communication capability can use the gateway 16 and any secondary device group 12a, 12b with a slave device 18 that includes wireless communication capability can dispense with use of the gateway 16. For example, the system 8 for automatically networking devices could include a first one of secondary device groups 12a with the gateway 16 and a second one of the secondary device groups 12b' without the gateway 16. The control device 20' of the system 8' for automatically networking devices could also be integrated with internal wireless communication software and hardware therein, thereby obviating a need for the gateway 16 (in other words, the control device 20 and the gateway 16 of the first embodiment are in a single housing).

Figure 2:
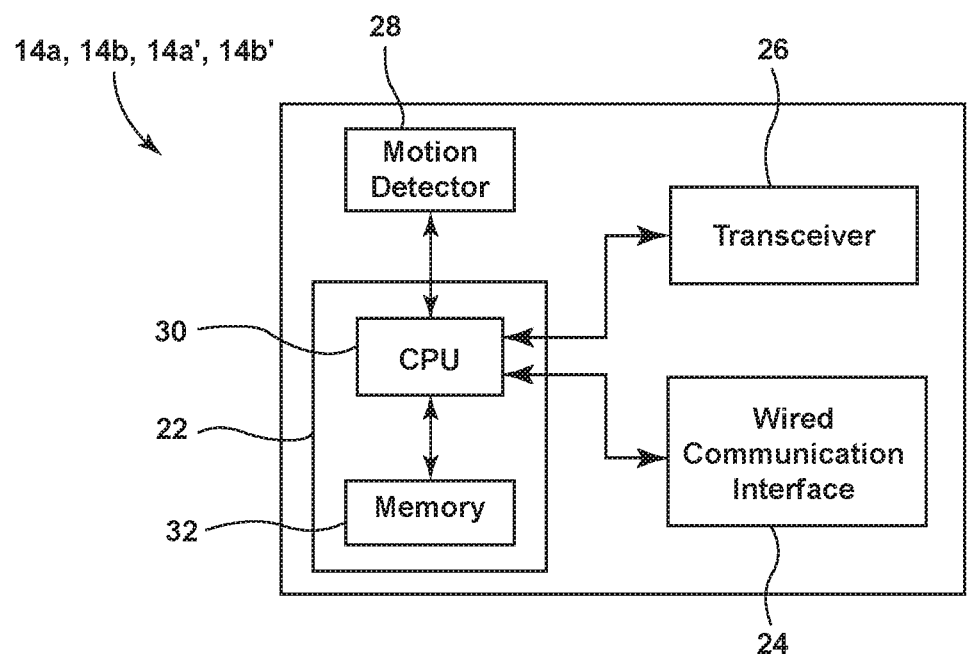
FIG. 2 is a schematic view of a wireless transceiver device embodying an aspect of the present invention.

In the illustrated example, the main wireless transceiver device 14a, 14a' and each of the secondary wireless transceiver devices 14b, 14b' (FIG. 2) facilitate establishment of the network. The main wireless transceiver device 14a, 14a' and each of the secondary wireless transceiver devices 14b, 14b' include a motherboard 22 having one or more processors 30 or other similar control devices as well as one or more memory devices 32. The processor 30 controls the overall operation of the wireless transceiver device 14a, 14a', 14b, 14b' and can include hardwired circuitry, programmable circuitry that executes software, or a combination thereof. The processor 30 may, for example, execute software stored in the memory device 32. The processor 30 may include, for example, one or more general- or special-purpose programmable microprocessors and/or microcontrollers, application specific integrated circuits (ASICs), programmable logic devices (PLDs), programmable gate arrays (PGAs), or the like. The memory device 32 may include any combination of one or more random access memories (RAMs), read-only memories (ROMs—which may be programmable), flash memory, and/or other similar storage devices. Each of the wireless transceiver devices 14a, 14a', 14b, 14b' also includes a wired communication interface 24 for physical connection with the slave devices 18, 18', a wireless transceiver 26 (or separate receiver and transmitter arrays) for communicating with other wireless transceiver devices 14a, 14a', 14b, 14b' and a motion detector 28. The motion detector 28 is employed to establish a network and to break at least a portion of the network as described below. The motion detector 28 can be any device used to sense motion of the wireless transceiver device 14a, 14a', 14b, 14b' and cessation of motion. For example, the motion detector 28 can be at least one accelerometer (e.g., linear and/or rotational), a vibration sensor or optical or image sensors that observe motion of the ground under the motion detector 28. It is contemplated that the motion detector 28 could be a separate device connected to the wireless transceiver device 14a, 14a', 14b, 14b'.

Figure 3:
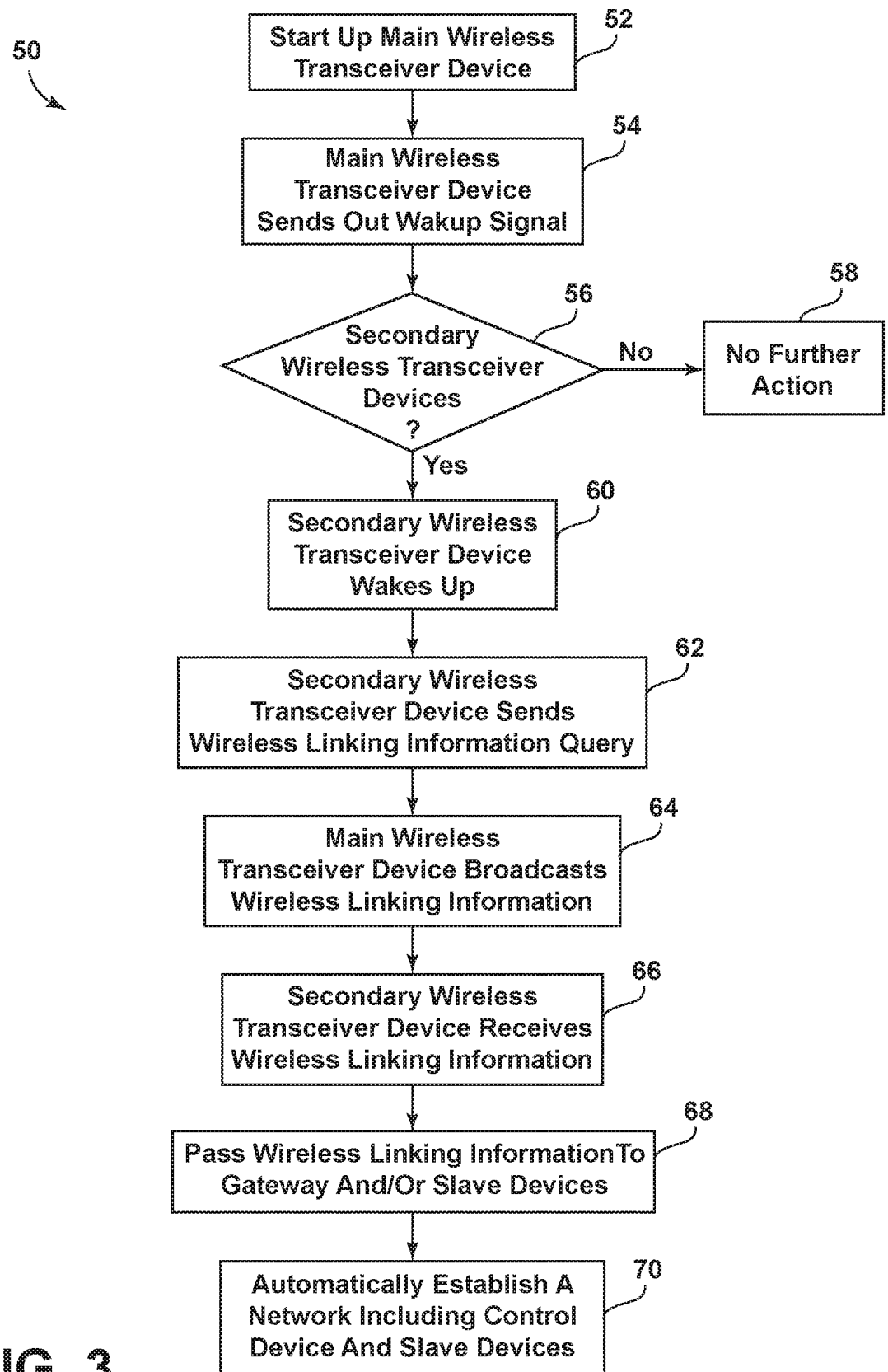
FIG. 3 illustrates a method of automatically establishing a network using the system for automatically networking devices.

FIG. 3 illustrates a method 50 of automatically establishing the network using the system 8, 8' for automatically networking devices. At initiation, the main wireless transceiver device 14a, 14a' of the main device group 10, 10' is booted up/started at step 52. The control device 20 and the gateway 16 or the control device 20' (which includes a built-in gateway 16) will also be booted up/started or already started at this point. Once fully booted up, the main wireless transceiver device 14a, 14a' will send out a wakeup broadcast received by any secondary wireless transceiver devices 14b, 14b' in the operating room at step 54. It is contemplated that the main wireless transceiver device 14a, 14a' can include a start button or icon that can be engaged to send out the wakeup broadcast of step 54 if the main wireless transceiver device 14a, 14a' is already booted up/started and one desires the method 50 to begin.

In the illustrated example, in order to only connect the slave devices 18, 18' in the secondary device group 12a, 12b, 12a', 12b' in the operating room 100 to the control device 20, 20' and not other slave devices 18, 18' outside of the operating room 100, the wakeup broadcast will only be sent and received within the operating room 100. The wakeup broadcast therefore will not pass through walls. For example, the wakeup broadcast can be sent by an infrared signal, an acoustic signal or radio waves (e.g., high frequency). It is contemplated that windows in the operating room 100 could include an optically-transparent, but infrared-blocking filter on the windows to stop or minimize light interference (e.g., sunlight) or crosstalk between window-connected rooms. It is also contemplated that the secondary wireless transceiver devices 14b, 14b' could use a signal processing approach such as low-pass filtering to only receive or process the wakeup broadcast from the main wireless transceiver device 14a, 14a' in the same operating room 100. If there are not any secondary wireless transceiver devices 14b, 14b' in the operating room 100 as determined at decision step 56, no further action is taken at this time at step 58 and the method 50 ends. It is further contemplated that the broadcast could be both infrared and ultrasonic. It is further contemplated that the devices receiving the broadcast signal would only process the broadcast signal if received both in infrared and ultrasonically to thereby ensure that only devices in the same room are communicating.

If there are secondary wireless transceiver devices 14b, 14b' in the operating room 100 as determined at decision step 56, the wakeup broadcast will wake up the secondary wireless transceiver devices 14b, 14b' in the operating room 100 at step 60. Once woken, the secondary wireless transceiver devices 14b, 14b' in the operating room 100 will send a wireless linking information query (e.g., IP and SSID) to the main wireless transceiver device 14a, 14a' at step 62. Once again, the wireless linking information query sent from the secondary wireless transceiver devices 14b, 14b' to the main wireless transceiver device 14a, 14a' will only be sent and received within the operating room 100 using the manner of communication as outlined above. The wireless linking information query therefore will not pass through walls or will be filtered using a signal processing approach. It is contemplated that the secondary wireless transceiver devices 14b, 14b' can also boot up/start the associated slave device(s) 18 and the associated gateway 16 or the associated slave device(s) 18' when woken at step 60.

The main wireless transceiver device 14a, 14a' will have the wireless linking information programmed therein or will be capable of obtaining the wireless linking information from the gateway 16 in the main device group 10 or from the control device 20'. The main wireless transceiver device 14a, 14a' will then broadcast the wireless linking information at step 64. It is contemplated that the secondary wireless transceiver device 14b, 14b' can also broadcast the wireless linking information if the wireless linking information query is received thereby. For example, the secondary wireless transceiver device 14b, 14b' can broadcast the wireless linking information every time the wireless linking information query is received or if the wireless linking information broadcast by the main wireless transceiver device 14a, 14a' is not received in a certain time period (for example, when the secondary wireless transceiver device 14b, 14b' sending the wireless linking information query is not capable of directly communicating with the main wireless transceiver device 14a, 14a'). Once again, the wireless linking information sent or broadcast to the second transceiver device 14b, 14b' will only be broadcast and received within the operating room 100 using the manner of communication as outlined above. The wireless linking information therefore will not pass through walls or will be filtered using a signal processing approach (or will be sent in another manner, for example, both in infrared and ultrasonically as outlined above). The second transceiver device 14*b*, 14*b*' then receives the wireless linking information at step 66 and passes the wireless linking information to the gateway 16 in the secondary device group 12*a*, 12*b* or the slave device 18' at step 68 to automatically establish a network including the control device 20 and the slave devices 18, 18' of the secondary device group 12*a*, 12*b*, 12*a*', 12*b*' at step 70.

Figure 4:
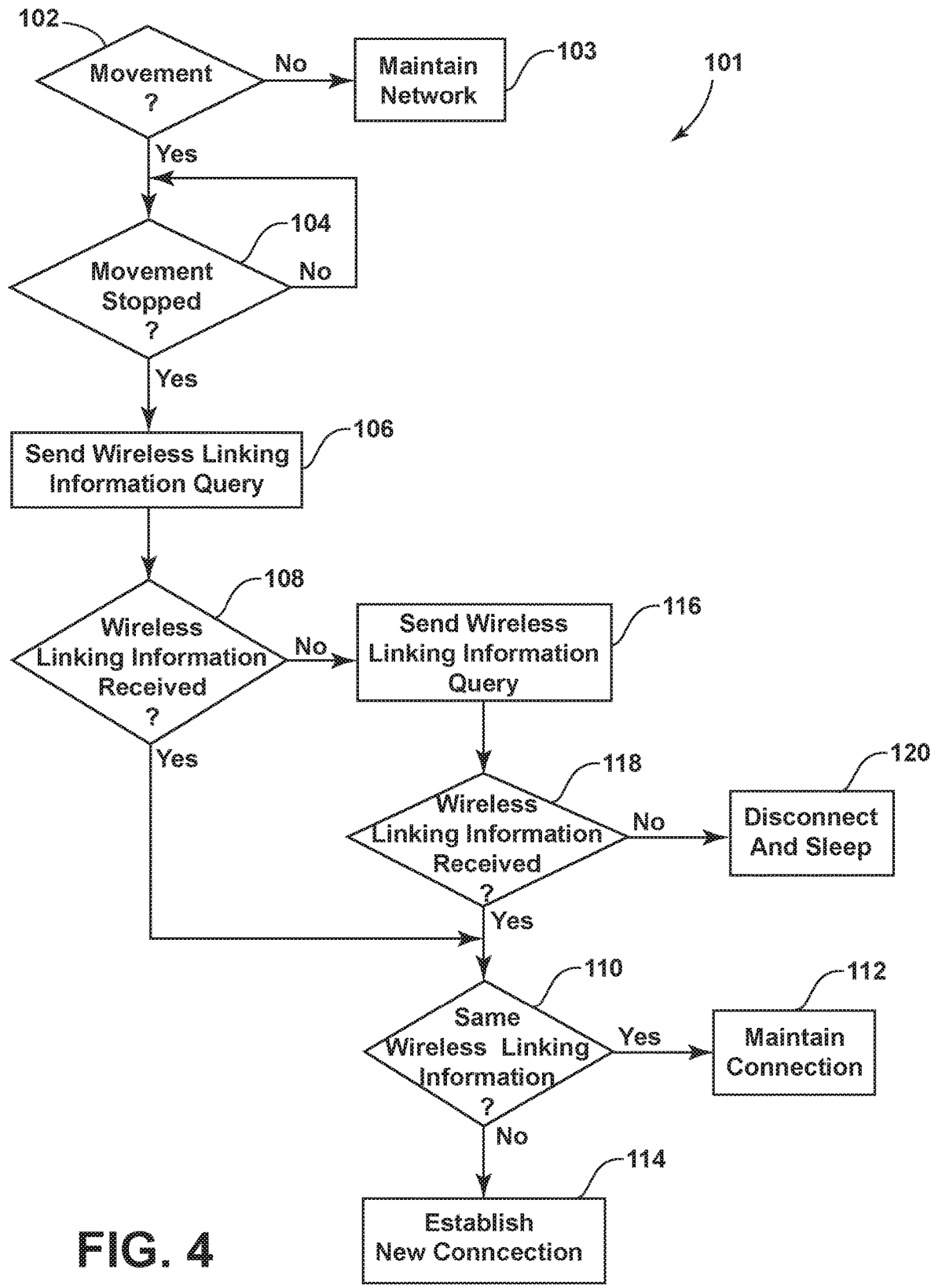
FIG. 4 illustrates a method for responding to movement of a secondary device group of the system for automatically networking devices.

FIG. 4 illustrates a method 101 for responding to movement of the secondary device group 12*a*, 12*b*, 12*a*', 12*b*'. As an initial step, there is a determination of whether the secondary device group 12*a*, 12*b*, 12*a*', 12*b*' has moved at decision step 102. Movement of the secondary device group 12*a*, 12*b*, 12*a*', 12*b*' can be determined using the motion detector 28 in the secondary wireless transceiver device 14*b*, 14*b*' as outlined above or can alternatively (or also) be determined using the signal processing approach outlined above (that is, low-pass filtering can determine if the secondary wireless transceiver device 14*b*, 14*b*' has moved when the signal goes below a certain threshold). If the motion detector 28 of the secondary wireless transceiver device 14*b*, 14*b*' does not send a signal that the secondary wireless transceiver device 14*b*, 14*b*' (and the corresponding secondary device group 12*a*, 12*b*, 12*a*', 12*b*') is moving to the processor 30 of the secondary wireless transceiver device 14*b*, 14*b*' at decision step 102, the network connection of the control device 20, 20' and the slave devices 18, 18' of the secondary device group 12*a*, 12*b*, 12*a*', 12*b*' is maintained at step 103. If the motion detector 28 of the secondary wireless transceiver device 14*b*, 14*b*' sends a signal that the secondary wireless transceiver device 14*b*, 14*b*' (and the corresponding secondary device group 12*a*, 12*b*, 12*a*', 12*b*') is moving to the processor 30 of the secondary wireless transceiver device 14*b*, 14*b*' at decision step 102, the method proceeds to decision step 104. At decision step 104, if the motion detector 28 of the secondary wireless transceiver device 14*b*, 14*b*' has not yet sent a signal that the secondary wireless transceiver device 14*b*, 14*b*' and the secondary device group 12*a*, 12*b*, 12*a*', 12*b*' have stopped moving to the processor 30 of the secondary wireless transceiver device 14*b*, 14*b*' (or continues to send a signal that the secondary wireless transceiver device 14*b*, 14*b*' continues to move), then the method 101 continues in a loop until the motion detector 28 of the secondary wireless transceiver device 14*b*, 14*b*' sends a signal that the secondary wireless transceiver device 14*b*, 14*b*' and the secondary device group 12*a*, 12*b*, 12*a*', 12*b*' have stopped moving to the processor 30 of the secondary wireless transceiver device 14*b*, 14*b*' (or discontinues sending a signal that the secondary wireless transceiver device 14*b*, 14*b*' is moving). Once a determination is made that the secondary wireless transceiver device 14*b*, 14*b*' is no longer moving at decision step 104, the secondary wireless transceiver device 14*b*, 14*b*' will send a wireless linking information query to the main wireless transceiver device 14*a*, 14*a*' at step 106.

If the secondary wireless transceiver device 14*b*, 14*b*' receives the wireless linking information at decision step 108, then a determination is made if the wireless linking information is identical to the wireless linking information currently in memory of the secondary wireless transceiver device 14*b*, 14*b*' at decision step 110. If the wireless linking information received in step 108 is identical to the wireless linking information currently in memory of the secondary wireless transceiver device 14*b*, 14*b*' as determined at decision step 110, the network connection of the control device 20, 20' and the slave devices 18, 18' of the secondary device group 12*a*, 12*b*, 12*a*', 12*b*' is maintained at step 112. If the wireless linking information received in step 108 is not identical to the wireless linking information currently in memory of the secondary wireless transceiver device 14*b*, 14*b*' as determined at decision step 110, the secondary wireless transceiver device 14*b*, 14*b*' erases the old wireless linking information and then passes the new wireless linking information to the gateway 16 in the secondary device group 12*a*, 12*b* or the slave device 18' at step 114 to automatically establish a new network between the control device 20, 20' and the slave devices 18, 18' of the secondary device group 12*a*, 12*b*, 12*a*', 12*b*' using the new wireless linking information at step 114. When decision step 110 determines that the wireless linking information received in step 108 is identical to the wireless linking information currently in memory of the secondary wireless transceiver device 14*b*, 14*b*', the secondary wireless transceiver device 14*b*, 14*b*' has only moved within the operating room 100 (e.g., jostled or moved to another area of the room). When decision step 110 determines that the wireless linking information received in step 108 is not identical to the wireless linking information currently in memory of the secondary wireless transceiver device 14*b*, 14*b*', the secondary wireless transceiver device 14*b*, 14*b*' has moved outside of the operating room 100 and into another operating room having another main wireless transceiver device 14*a*, 14*a*'.

If the secondary wireless transceiver device 14*b*, 14*b*' does not receive the wireless linking information at decision step 108, then the secondary wireless transceiver device 14*b*, 14*b*' will send another wireless linking information query at step 116 after a certain predetermined time period (e.g., 1 minute). If the secondary wireless transceiver device 14*b*, 14*b*' receives the wireless linking information at decision step 118 after sending out another wireless linking information query at step 116, then the method proceeds to decision step 110 as outlined above. If the secondary wireless transceiver device 14*b*, 14*b*' does not receive the wireless linking information at decision step 118 after sending out another wireless linking information query at step 116, then the secondary wireless transceiver device 14*b*, 14*b*' will instruct the gateway 16 in the secondary device group 12*a*, 12*b*, 12*a*', 12*b*' or the slave device 18' (with the integrated gateway 16) to set the network ID to "not current" and go into sleep mode at step 120. It is also contemplated that the secondary wireless transceiver device 14*b*, 14*b*' could also instruct the gateway 16 in the secondary device group 12*a*, 12*b*, 12*a*', 12*b*' or the slave device 18' (with the integrated gateway 16) to go into sleep mode. It is contemplated that steps 116 and 118 can be performed more than once (e.g., 3 times or every certain time interval (e.g., every 2-3 seconds) for a certain period of time (e.g., 1 minute)) before proceeding to step 120 if the secondary wireless transceiver device 14*b*, 14*b*' continues to not receive the wireless linking information. Once the secondary wireless transceiver device 14*b*, 14*b*' is in sleep mode, the secondary wireless transceiver device 14*b*, 14*b*' can continue in sleep mode until the main wireless transceiver device 14*a*, 14*a*' sends out a wakeup signal as outlined in step 54 of method 50 above. It is also contemplated that the secondary wireless transceiver device 14*b*, 14*b*' can be manually woken to send out the wireless linking information query as set forth in step 60 of method 50 above (e.g., automatically sent when powered on), thereby bypassing the need for the main wireless transceiver device 14*a*, 14a' to send out the wake up signal. Moreover, the secondary wireless transceiver device 14b, 14b' can be programmed to periodically wake up (e.g., every 2 hours) to send out the wireless linking information query and go back to sleep if no wireless linking information broadcast is received.

Figure 5:
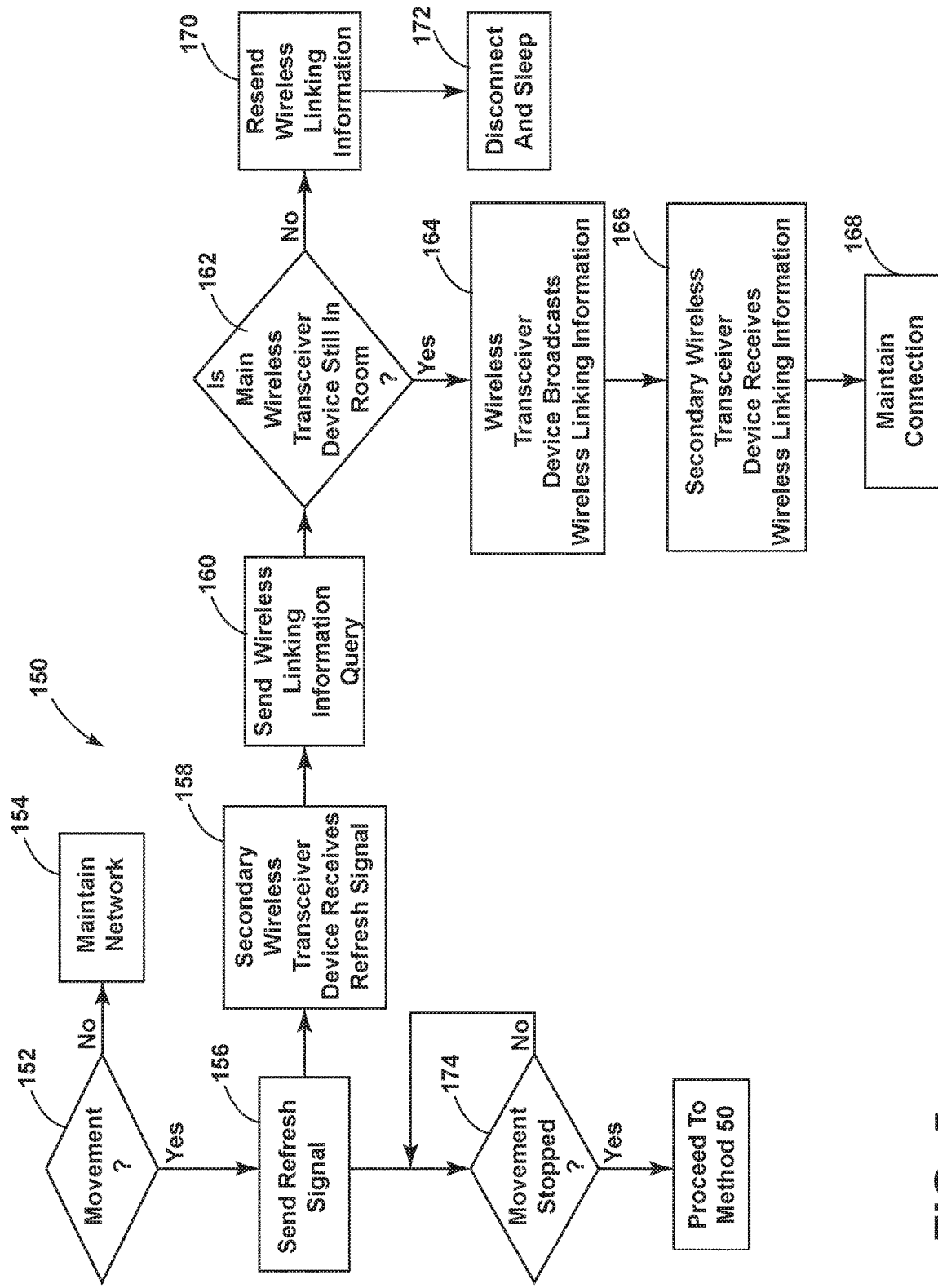
FIG. 5 illustrates a method for responding to movement of a main device group of the system for automatically networking devices.

FIG. 5 illustrates a method 150 for responding to movement of the main device group 10, 10'. As an initial step, there is a determination of movement of the main device group 10, 10' at decision step 152. Movement of the main device group 10 is determined using the motion detector 28 in the main wireless transceiver device 14a or using a signal processing approach as outlined above. If the motion detector 28 of the main wireless transceiver device 14a, 14a' does not send a signal that the main wireless transceiver device 14a, 14a' and thereby the main device group 10, 10' is moving to the processor 30 of the main wireless transceiver device 14a, 14a' at decision step 152, the network connection of the control device 20, 20' and the slave devices 18, 18' of the secondary device group 12a, 12b, 12a', 12b' is maintained at step 154. If the motion detector 28 of the main wireless transceiver device 14a, 14a' sends a signal that the main wireless transceiver device 14a, 14a' and thereby the main device group 10, 10' is moving to the processor 30 of the main wireless transceiver device 14a, 14a' at decision step 152, then the method proceeds to step 156 wherein the main wireless transceiver device 14a, 14a' sends out a refresh signal. The refresh signal can be sent via Wi-Fi (e.g., through the gateway 16, 16') or directly from the main wireless transceiver device 14a, 14a' via the communication techniques outlined above. The main wireless transceiver device 14a, 14a' sends out a refresh signal at step 156 when movement of the main wireless transceiver device 14a, 14a' begins.

The secondary wireless transceiver devices 14b, 14b' in the operating room 100 will receive the refresh signal at step 158 and then determine if the main wireless transceiver device 14a, 14a' and the main device group 10, 10' have left the operating room 100. First, at step 160, the secondary wireless transceiver devices 14b, 14b' will send a wireless linking information query to the main wireless transceiver device 14a, 14a' after a set period of time (e.g., 1 minute) at step 160. If the main wireless transceiver device 14a, 14a' is still in the operating room 100 as determined at decision step 162, the main wireless transceiver device 14a, 14a' will broadcast the wireless linking information at step 164. The secondary wireless transceiver device 14b, 14b' will receive the wireless linking information broadcast at step 166 and the network connection of the control device 20, 20' and the slave devices 18, 18' of the secondary device group 12a, 12b, 12a', 12b' is maintained at step 168.

If the main wireless transceiver device 14a, 14a' is no longer in the operating room 100 as determined at decision step 162, then the secondary wireless transceiver device 14b, 14b' will send another wireless linking information query at step 170 after a certain predetermined time period (e.g., 1 minute) or for a certain period of time. Since the main wireless transceiver device 14a, 14a' is no longer in the operating room 100, the secondary wireless transceiver device 14b, 14b' will instruct the gateway 16 in the secondary device group 12a, 12b or the slave device 18' to set the network ID to "not current" and go into sleep mode at step 172. It is also contemplated that the secondary wireless transceiver device 14b, 14b' could also instruct the gateway 16 in the secondary device group 12a, 12b or the slave device 18' to go into sleep mode. Further, step 170 can be performed more than once (e.g., 3 times or every certain time interval (e.g., every 2-3 seconds) for a certain period of time (e.g., 1 minute)) before proceeding to step 172 if the secondary wireless transceiver device 14b, 14b' continues to not receive the wireless linking information. Once the secondary wireless transceiver device 14b, 14b' is in sleep mode, the secondary wireless transceiver device 14b, 14b' will continue in sleep mode until the main wireless transceiver device 14a, 14a' sends out a wakeup signal as outlined in step 54 of method 50 above. The secondary wireless transceiver device 14b, 14b' can be manually woken (e.g., automatically sent when powered on) to send out the wireless linking information query as set forth in step 60 of method 50 above, thereby bypassing the need for the main wireless transceiver device 14a, 14a' to send out the wake up signal. The secondary wireless transceiver device 14b, 14b' could send out the wireless linking information query more than once at step 160 when the main wireless transceiver device 14a, 14a' is still in the operating room 100 if the secondary wireless transceiver device 14b does not receive the control IP broadcast from the main wireless transceiver device 14a, 14a' during the initial broadcast (or if the main wireless transceiver device 14a, 14a' does not receive the first wireless linking information query (or first couple wireless linking information queries)).

After the main wireless transceiver device 14a sends out the refresh signal at step 156, the method 150 proceeds to decision step 174. At decision step 174, if the motion detector 28 of the main wireless transceiver device 14a, 14a' has not yet sent a signal that the main wireless transceiver device 14a, 14a' and the associated main device group 10 have stopped moving to the processor 30 of the main wireless transceiver device 14a, 14a' (or continues to send a signal that the main wireless transceiver device 14a continues to move), then the method 150 continues in a loop until the motion detector 28 of the main wireless transceiver device 14a, 14a' sends a signal that the main wireless transceiver device 14a, 14a' and the main device group 10, 10' have stopped moving to the processor 30 of the main wireless transceiver device 14a, 14a' (or discontinues sending a signal that the main wireless transceiver device 14a, 14a' is moving). Once a determination is made that the main wireless transceiver device 14a, 14a' is no longer moving at decision step 174, the method 150 for responding to movement of the main device group 10 proceeds to the method 50 of automatically establishing the network using the system 8, 8' for automatically networking devices. It is contemplated that step 52 of the method 50 of automatically establishing the network using the system 8, 8' for automatically networking devices could be omitted at this step if the main wireless transceiver device 14a, 14a' is already running. It is further contemplated that the main wireless transceiver device 14a, 14a' could send out a "movement stop" message, which will cause the secondary wireless transceiver devices 14b, 14b' to go to decision step 110 of the method of FIG. 4.

Figure 6:
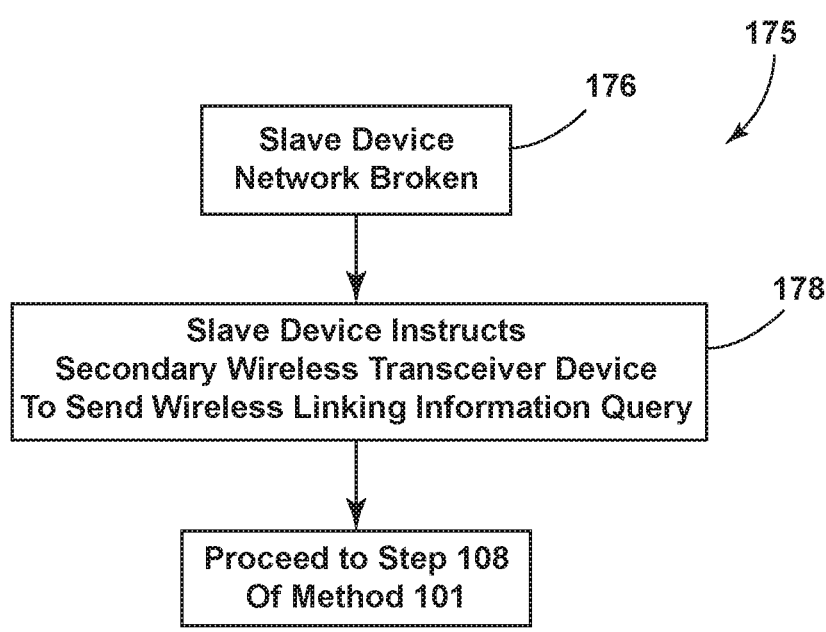
FIG. 6 illustrates a method for responding to loss of a network signal by the secondary device group of the system for automatically networking devices.

FIG. 6 illustrates a method 175 for responding to loss of a network signal by the secondary device group 12a, 12b, 12a', 12b' of the system 8, 8' for automatically networking devices. Starting at step 176, the wireless network including the slave device 18, 18' is broken (that is, the slave device 18, 18' and/or the gateway 16 no longer is receiving any signals from the gateway 16 connected to the control device 20 or from the control device 20'). The slave device 18, 18' will then instruct the secondary wireless transceiver device 14b, 14b' to transmit a wireless linking information query at step 178. Once the secondary wireless transceiver device 14b, 14b' transmits the wireless linking information query at step 178, the method 175 for responding to loss of a network signal proceeds to step 108 of the method 101 as outlined above and proceeds through the rest of the steps of method 101 (including steps 110, 112, 114, 116, 118 and/or 120 as determined using the methodology of method 101 outlined above).

Figure 7:
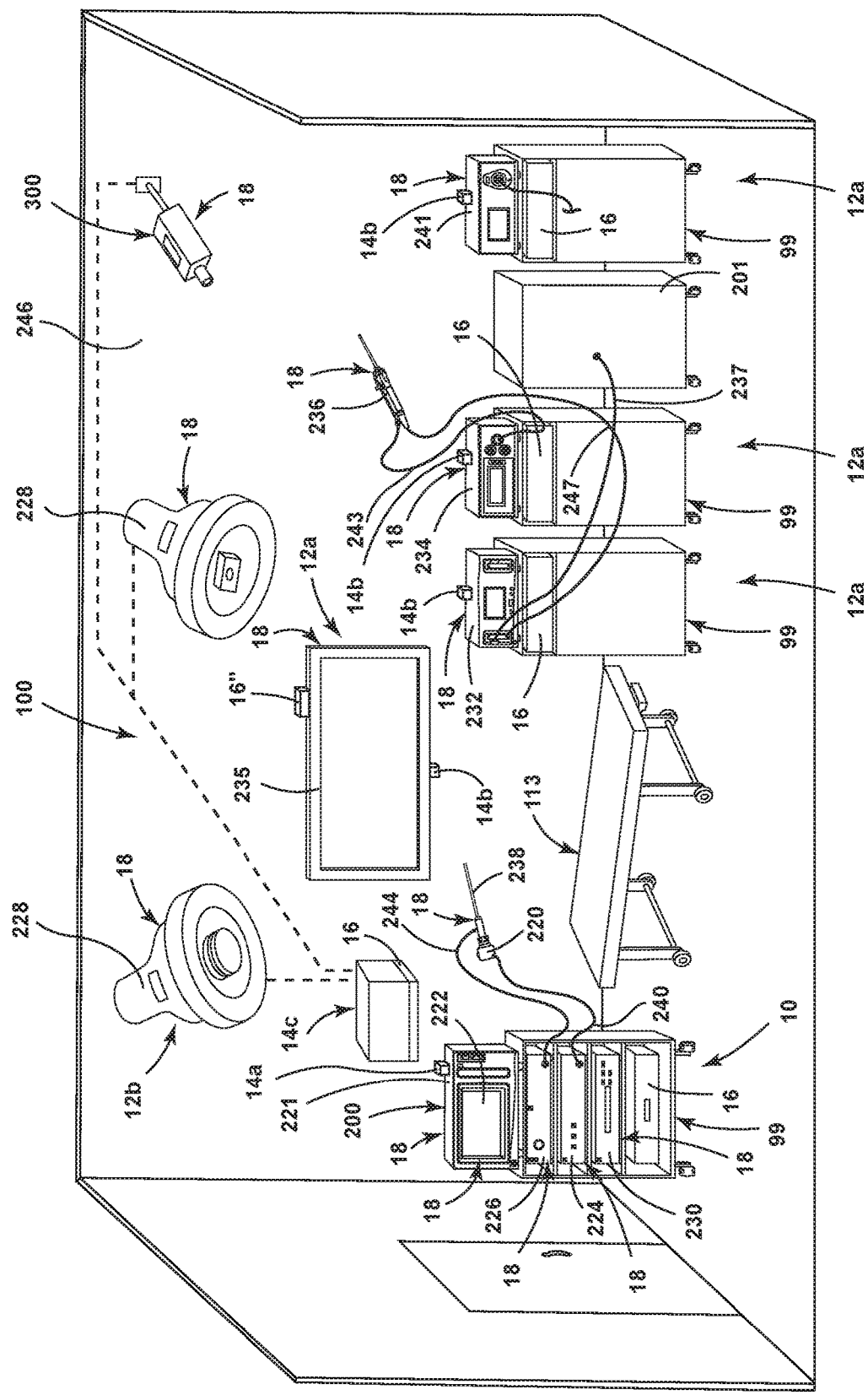
FIG. 7 is a perspective view of an operating room illustrating examples of configurable devices.

FIG. 7 depicts a perspective view of an operating room 100 according to one embodiment illustrating specific examples of the slave devices 18, 18'. The operating room 100 includes a surgical table 113 configured to support a patient thereon during surgery and a plurality of the slave devices 18, 18' used for performing or assisting in surgery on the patient within the operating room 100. The control device 20, 20' can control the functions of the slave devices 18, 18'. However, it is contemplated that the slave devices 18, 18' can also or alternatively be independently controlled.

As illustrated in FIG. 7, examples of slave devices 18 include an image and video capture and recording device 200, a video camera 220 and an associated endoscope 238, a touchscreen monitor 222, a camera control unit 224, a scope light source unit 226, operating room lights 228, a printer 230, a fluid management pump 232, an insufflator 241, a shaver 236, an RF and shaver control 234 and an additional monitor 235. However, any slave device 18 located within the operating room 100 can receive instruction from the control device 20, 20'. The slave devices 18 are illustrated as being part of a main device group 10 and part of secondary device groups 12a provided on the carts 99. The main device group 10 and the secondary device groups 12a are illustrated as including a separate gateway 16 as outlined above. However, the slave devices 18 and the control device 20 could have the gateway 16 incorporated therein as outlined above, thereby obviating the need for a separate gateway 16 (that is, the slave devices and the control device could be the slave devices 18' and the control device 20' outlined above). The operating room 100 also includes a secondary device group 12b including a room master wireless transceiver device 14c and a gateway 16". The room master wireless transceiver device 14c is fixed in position within the operating room 100 and is identical to the main wireless transceiver device 14a, 14a' and the secondary wireless transceiver devices 14b, 14b' outlined above, although the room master wireless transceiver device 14c does not require a motion detector 28 as the room master wireless transceiver device 14c is not intended to move. The room master wireless transceiver device 14c can be wired to the gateway 16 and the gateway 16 can be wired to slave devices 18 which are normally fixed in the operating room 100 (e.g., the operating room lights 228 and a room camera 300). It is contemplated that the secondary wireless transceiver device 14b, 14b' could be the room master wireless transceiver device 14c (i.e., the secondary wireless transceiver device 14b, 14b' could be fixed in position in the operating room 100 along with the rest of the main device group 10 (e.g., on shelving)). The room master wireless transceiver device 14c is discussed in more detail below in regard to FIG. 8.

In the illustrated example, one of the slave devices 18 is the image and video capture and recording device 200 located in a control housing 221. The image and video capture and recording device 200 can output images and video on the touchscreen monitor 222, which can be integrated into the control housing 221. The image and video capture and recording device 200 can also output images and video to the additional monitor 235 via either a wired connection or wirelessly (e.g., to another slave device 18, 18'). The illustrated image and video capture and recording device 200 is therefore capable of displaying images and videos on the touchscreen monitor 222 and/or on the additional monitor 235 captured live by cameras and/or replayed from recorded images and videos. The image and video capture and recording device 200 can also control the images and videos being shown on the touchscreen monitor 222 (e.g., by controlling the source of the image on the touchscreen monitor 222 (e.g., from a camera, from a saved video file, etc.)).

The illustrated image and video capture and recording device 200 is also capable of recording images and videos. The image and video capture and recording device 200 can include an internal hard drive for storing captured images and videos and can also communicate with a picture archiving and communication system (PACS), as is well known to those skilled in the art, to save images and video in the PACS and for retrieving images and videos from the PACS. The image and video capture and recording device 200 can also display any saved images (e.g., from the internal hard drive or from the PACS) on the touchscreen monitor 222 and/or the additional monitor 235. It is contemplated that the image and video capture and recording device 200 could obtain or create images of a patient during a surgical procedure from a variety of sources (e.g., from video cameras, video cassette recorders, X-ray scanners (which convert X-ray films to digital files), digital X-ray acquisition apparatus, fluoroscopes, CT scanners, MRI scanners, ultrasound scanners, CCD devices, and other types of scanners (handheld or otherwise)). The image and video capture and recording device 200 having the touchscreen monitor 222 within the control housing 221 is well known to those skilled in the art. An example of an image and video capture and recording device 200 is the SDC3 HD Information Management System as sold by Stryker Corporation of Kalamazoo, Mich. An example of an additional monitor 235 is the WISE HDTV wireless display as sold by Stryker Corporation of Kalamazoo, Mich. The additional monitor 235 can be wired to the image and video capture and recording device 200 or can be wirelessly connected (e.g., by using the Wireless WISE HD transmitter as sold by Stryker Corporation of Kalamazoo, Mich.).

In the illustrated example, several of the slave devices 18 can be controlled by the image and video capture and recording device 200 for obtaining the images and videos and for outputting the captured and recorded images and videos. For example, the images and videos can be captured by the video camera 220, which includes well-known components for generating color video based on light received through the endoscope 238 of the type commonly used for laparoscopy or arthroscopy (e.g., endoscope). The image and video capture and recording device 200 can control the video camera 220 to turn on and turn off the video camera 220 or to capture images using the video camera 220. The control device 20 can communicate with the video camera 220 to adjust settings of the video camera 220 (e.g., resolution, zoom, etc.).

Yet another slave device 18 is the camera control unit 224 that is coupled to the video camera 220 by a flexible electronic transmission line 240. The transmission line 240 conveys video data from the video camera 220 to the camera control unit 224 and also conveys various control signals bi-directionally between the video camera 220 and the camera control unit 224. The camera control unit 224 can be connected (wired or wirelessly) to the image and video capture and recording device 200 to provide the images and videos to the image and video capture and recording device 200. Video cameras 220 and camera control units 224 used with endoscopes 238 are well known to those skilled in the art. An example of the video camera 220 and camera control unit 224 for use with an endoscope is the 1488 HD Camera as sold by Stryker Corporation of Kalamazoo, Mich.

Another slave device 18 is the scope light source unit 226 that transmits high intensity light into the patient through the endoscope 238 via a fiber optic cable 244. Scope light source units 226 used with endoscopes 238 are well known to those skilled in the art. An example of the scope light source unit 226 for use with the endoscope 238 is the L9000 LED Light Source as sold by Stryker Corporation of Kalamazoo, Mich.

Another of the plurality of slave devices 18 can include the operating room lights 228 mounted to one of the ceilings, a room wall 246 or other stationary structure of the operating room 100. The control device 20 can be used to adjust the intensity of the operating room lights 228. Yet another slave device 18 can be the room camera 300 mounted to one of the ceiling, a room wall 246 or other stationary structure of the operating room 100.

Yet another one of the plurality of slave devices 18 is the printer 230. The printer 230 can be connected to the image and video capture and recording device 200 for outputting images from the image and video capture and recording device 200. The control device 20 can control the printer 230 in order to print selected images. An example of the printer 230 is the SDP1000 Medical Grade Digital Printer as sold by Stryker Corporation of Kalamazoo, Mich.

Another of the plurality of slave devices 18 is the fluid management pump 232. The fluid management pump 232 is employed during surgical procedures to introduce sterile solution into the surgical site and to remove fluid and debris generated by the procedure. In the illustrated example, the fluid management pump 232 can supply the motive force for pumping the sterile solution through an inflow tube (not shown) into the surgical site via a cannula. The fluid management pump 232 can also supply the motive force for suctioning solution and any waste material removed from the surgical site from an outflow tube 247 to a waste tube 237 connected to a waste container 201. In the illustrated example, the outflow tube 247 is connected to the shaver 236. An example of the fluid management pump 232 is disclosed in U.S. Patent Application Publication No. 2013/0267779 entitled CONTROL FOR SURGICAL FLUID MANAGEMENT PUMP SYSTEM, the entire contents of which are hereby incorporated herein by reference. An example of the shaver 236 is the FORMULA® Shaver Hand Piece as sold by Stryker Corporation of Kalamazoo, Mich. The control device 20 can control the fluid management pump 232 by altering various controls of the control unit for the fluid management pump 232. For example, the control device 20 can control the pressure of the fluid being pumped into the surgical site and/or the flow rate of fluid to or from the surgical site. The control device 20 can also control the speed of the shaver 236 or other settings.

Yet another one of the plurality of slave devices 18 is the RF and shaver control 234. The RF and shaver control 234 sends power to an ablation and coagulation device or electrosurgical tool (not shown) and/or the shaver 236. Ablation and coagulation devices are well known to those skilled in the art. An example of an ablation and coagulation device that can be connected to the RF and shaver control 234 is the SERFAS™ Energy Probe as sold by Stryker Corporation of Kalamazoo, Mich. The RF and shaver control 234 sends power to the shaver 236 through a cable 243. An example of the RF and shaver control 234 is the CROSSFIRE® arthroscopic resection system as sold by Stryker Corporation of Kalamazoo, Mich. The control device 20 can control the RF and shaver control 234 by altering the power sent to the ablation and coagulation device (not shown) and/or the shaver 236 or other controls.

Another of the plurality of slave devices 18 is the insufflator 241. The insufflator 241 is used to supply inert, nontoxic gases, such as carbon dioxide, into a body cavity, in order to expand the cavity, or to minimize visual obstruction during minimally invasive or laparoscopic surgery. An insufflator 241 is well known to those skilled in the art. An example of the insufflator 241 is the PNEUMOSURE® 45L Insufflator as sold by Stryker Corporation of Kalamazoo, Mich. The control device 20 can control the insufflator 241 by adjusting the pressure of the gas supplied into the body cavity.

The control device 20 can have a motherboard that includes one or more processors or other similar control devices as well as one or more memory devices. The processor controls the overall operation of the control device and can include hardwired circuitry, programmable circuitry that executes software, or a combination thereof. The processor may, for example, execute software stored in the memory device. The processor may include, for example, one or more general- or special-purpose programmable microprocessors and/or microcontrollers, application specific integrated circuits (ASICs), programmable logic devices (PLDs), programmable gate arrays (PGAs), or the like. The memory device may include any combination of one or more random access memories (RAMs), read-only memories (ROMs) (which may be programmable), flash memory, and/or other similar storage devices. The control device 20 can also have a network interface for connecting the control device 20 to the Internet or other type of wide area network (WAN), a local area network (LAN), a corporate intranet, any other type of network, or a combination of such networks.

The illustrated control device 20 can be a stand-alone device communicating with the slave devices 18 (wired or wirelessly) to control the slave devices 18 and to configure the slave devices 18 by adjusting the settings of the slave devices 18. Alternatively, the control device 20 can be incorporated into one of the slave devices 18 that communicates with the other slave devices 18 to control the other slave devices 18 and to configure the slave devices 18 by adjusting the settings of the slave devices 18. In the illustrated example, the control device 20 can be incorporated within the control housing 221 of the image and video capture and recording device 200 such that the touchscreen monitor 222 can be used to control the slave devices 18. It is further contemplated that the image and video capture and recording device 200 can control slave devices 18, 18' via the touchscreen 222 and also can receive audible or voice commands to control the slave devices 18, 18'. The control device 20, 20' can have input devices connected thereto (e.g., foot switch) to issue any commands to the slave devices 18, 18' (e.g., triggering the foot switch can capture digital images from the video camera 220). An example of a control device 20, 20' interacting with slave devices 18, 18' for controlling the slave devices 18, 18' is the SDC3 HD Information Management System (with device control and/or voice device control) as sold by Stryker Corporation of Kalamazoo, Mich. Further, such a control device is also disclosed in U.S. Patent Application Publication No. 2012/0274586 entitled METHOD AND APPARATUS FOR INTEGRATING MULTIPLE APPLICATIONS ON A SINGLE TOUCH PANEL, the entire contents of which are hereby incorporated herein by reference.

Figure 8:
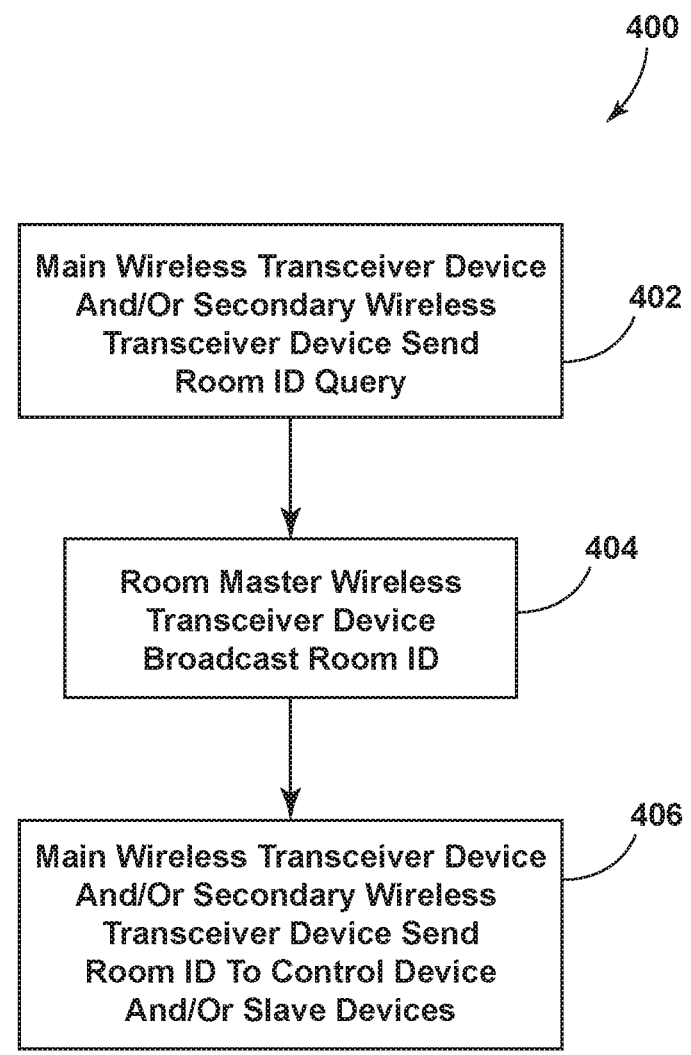
FIG. 8 illustrates a method for sending out room specific information using the system for automatically networking devices.

FIG. 8 illustrates a method 400 for sending out room specific information using the system for automatically networking devices 8, 8'. For the method 400, the room master wireless transceiver device 14c is needed. In the method 400, the main wireless transceiver device 14a, 14a' and/or the secondary wireless transceiver device 14b, 14b' sends out the wireless linking information query and/or a room ID query at step 402. Step 402 can happen when the main wireless transceiver device 14a, 14a' and/or the secondary wireless transceiver device 14b, 14b' are powered up or when motion of the main wireless transceiver device 14a, 14a' and/or the secondary wireless transceiver device 14b, 14b' has stopped. In response to the wireless linking information query and/or a room ID query, the room master wireless transceiver device 14c will broadcast the room ID specific to the operating room 100 having the room master wireless transceiver device 14c therein at step 404. The main wireless transceiver device 14a, 14a' and/or the secondary wireless transceiver device 14b, 14b' will then send the room ID to the control device 20, 20', the gateway 16 and/or the slave devices 18, 18' (e.g., through the gateway 16) at step 406. The room master wireless transceiver device 14c can have the room ID programmed therein or can obtain the room ID from another device fixed in the operating room 100 (e.g., the control device 20, 20') that has the room ID programmed therein.

In the illustrated example, the room ID can be used to obtain information about the location of the devices in the operating room 100. For example, the slave devices 18, 18', the control device 20, 20', the wireless transceiver devices 14a, 14b, 14a', 14b', the room master wireless transceiver device 14c and/or the device groups 10, 10', 12a, 12b, 12a', 12b' can send location information to a central computing system of the medical complex informing the central computing system of the presence of all devices within an operating room 100 associated with a particular room ID (automatically or after request from the central computing system of the medical complex). The location information can include a device ID unique to each device along with a room ID. Therefore, the location of the devices in the medical complex can be accurately tracked in real time.

The room ID obtained in the illustrated example can also be used to configure the operating room 100 and/or obtain information about the devices in the operating room 100. For example, the control device 20, 20' can connect to a hospital scheduling system and electronic medical records to automatically configure the control device 20, 20' and the slave devices 18, 18' in the operating room 100 for the next surgery to be performed in the operating room 100 identified with the room ID. It is contemplated that only the slave devices 18, 18' to be used in the next surgery will be configured. For example, the control device 20, 20' and the slave devices 18, 18' can be automatically configured for the particular surgery to be performed, the particular patient and/or for the particular medical staff that will be performing the medical operation in the operating room 100 identified with the room ID at a particular time. The configurations to be used can be obtained from a digital surgical preference card saved in the medical facility's IT system (e.g., EMR record system). Moreover, the digital surgical preference card can be updated after surgery from information obtained during surgery by having the control devices 20, 20' send the updated information to the medical facility's IT system. Using the room ID, it is possible to transport the device groups 10, 12a, 12b into a particular operating room 100 and have the slave devices 18, 18' be automatically configured once powered. It is also contemplated that the devices in the operating room 100 can be configured by obtaining preferences using the METHOD OF CONFIGURING DEVICES IN AN OPERATING THEATER as disclosed in U.S. Provisional Patent Application No. 62/100,286, the entire contents of which are hereby incorporated herein by reference. The METHOD OF CONFIGURING DEVICES IN AN OPERATING THEATER can be used employing the room ID or can be used without knowing the room ID using the methods disclosed in U.S. Provisional Patent Application No. 62/100,286.

In the illustrated example, the slave devices 18, 18' can be further configured using the room ID. For example, the control device 20, 20' can select appropriate monitor and camera settings (e.g., color setpoint) based on the particular surgery to be performed, the particular patient and/or for the particular medical staff and/or can use an algorithm that allows the system 8, 8' to learn the appropriate settings based on the particular surgery to be performed, the particular patient and/or for the particular medical staff. Moreover, the monitors 222, 235 can be adjusted to suit the brightness, resolution, color balance and other image parameter preferences of a member of the medical staff using the particular room before the surgical procedure begins using information associated with the medical procedure schedule associated with the room ID. Likewise, video equipment can be configured with appropriate surgical specialty parameters, post-processing method, and light and gain level before the surgical procedure begins using information associated with the medical procedure schedule associated with the room ID. Moreover, when the slave devices 18, 18' include surgical tools (e.g., the shaver 236), the slave devices 18, 18' can be configured with energy, speed, mode and suction parameters to be used for the particular procedure scheduled in the operating room 100 at a particular time using information associated with the medical procedure schedule associated with the room ID. Furthermore, an audio system in the operating room 100 can play music of choice of the medical staff and at a selected volume using information associated with the medical procedure schedule associated with the room ID.

The illustrated slave devices 18, 18' can further be configured without the need to know the room ID. For example, the system 8, 8' can be used to configure the setting of the scope light source unit 226, insufflator 241, fluid management pump 232 or video camera 220 settings based on actions of connected slave devices 18, 18' to obtain the best possible image in the presence of active instruments (e.g., a particular cutter or endoscope). Moreover, slave devices 18, 18' on carts 99 can receive software updates automatically from control devices 20, 20' connected to the existing hospital network. Real time monitoring and troubleshooting of the slave devices 18, 18' on the carts 99 can be performed from outside a sterile field and potentially from a remote workstation.

The room ID obtained in the illustrated example can also be used to send information to be used by the devices in the operating room 100 or to record information from the devices in the operating room 100. For example, digital capture documentation (for example, for the image and video capture and recording device 200) can be automatically retrieved from the electronic medical records and fields therein can be automatically populated. For example, information about the patient, medical professional and procedure can be obtained using the room ID to automatically populate intra-surgical documentation as disclosed in U.S. Provisional Patent Application No. 62/061,398 entitled INTRA-SURGICAL DOCUMENTATION SYSTEM, the entire contents of which are hereby incorporated herein by reference. Furthermore, all captured data, imagery and video can be automatically recorded in the record (such as an electronic health record system) associated with a particular patient in the operating room 100 identified with the room ID at a particular time upon completion of the procedure. Moreover, it can be possible to query the patient medical record and notify the medical staff of any safety issues important to the medical procedure or the instruments used in the medical procedure.

In the illustrated example, the system 8, 8' can be used to send log information (e.g., hours of usage, type of usage, operation information) for the slave devices 18, 18' to a central computing system of the medical facility or the control device 20, 20' for storage, use and/or analysis at a later time. The log information can be sent to the central computing system automatically or after the central computing system sends a query to the slave devices 18, 18' through the network including the slave devices 18, 18' (e.g., when the existing hospital network is connected to the control device 20, 20'). The log information sent to the central computing system or the control device 20, 20' provides a possibility for automatically notifying and triggering a corrective response (e.g., from sales or engineering staff) when a minor issue first arises. The corrective response can resolve issues before the issues are noticed by the medical staff. The log information can also be used for automated pay-per-use billing of use of the slave devices 18, 18'.

In the illustrated example, the secondary wireless transceiver devices 14b, 14b', the main wireless transceiver devices 14a, 14a' and the room master wireless transceiver device 14c all communicate with each other in the same operating room 100. To facilitate this communication, it is contemplated that all of the broadcasts (e.g., the refresh signal, the room ID and the wireless linking information) from the main wireless transceiver devices 14a, 14a' (e.g., the refresh signal, the room ID and the wireless linking information) or the room master wireless transceiver device 14c (e.g., the room ID) can be echoed by each secondary wireless transceiver device 14b, 14b' that received such broadcast to ensure that every secondary wireless transceiver device 14b, 14b' in the operating room 100 receives the broadcast. Furthermore, it is contemplated that all of the secondary wireless transceiver devices 14b, 14b', the main wireless transceiver devices 14a, 14a' and the room master wireless transceiver device 14c be installed in or positioned at a fixed vertical height range from the ground. Moreover, it is contemplated that the transmitting portion of the wireless transceiver 26 (e.g., LEDs) can point radially outward in a horizontal plane to create a toroidal far-field beam pattern and that the receiving portion of the wireless transceiver 26 (e.g., infrared receiver integrated circuit) can be located on a radial edge of the circuit board of the devices 14a, 14a', 14b, 14b' and 14c on the opposite side of the transmitting portion to maximize the view field and sensitivity of the receiving portion while minimizing saturation of the receiving portion from light emitted from the transmitting portion of the same device 14a, 14a', 14b, 14b' and 14c.

It is possible for the secondary wireless transceiver devices 14b, 14b' in the illustrated example to lose the network connection. For example, the main wireless transceiver devices 14a, 14a' could move outside of the operating room 100 as outlined above in regard to the method 150 of FIG. 5. However, if the secondary wireless transceiver devices 14b, 14b' lose the network connection without the main wireless transceiver devices 14a, 14a' having been moved, it is contemplated that the secondary wireless transceiver devices 14b, 14b' can perform a portion of method 101 starting at step 106 to reestablish connection (or enter the sleep mode if appropriate).

The illustrated secondary wireless transceiver devices 14b, 14b' can send wireless linking information queries or room ID queries at certain time periods or for limited times to preserve power and to minimize signal traffic. Therefore, the secondary wireless transceiver devices 14b, 14b' can send the query messages no more frequently than a fixed time interval (e.g., 1 minute as outlined above) or a random time interval (1) from transmission of a signal by the particular secondary wireless transceiver device 14b, 14b', (2) from reception of a signal from another wireless transceiver devices 14a, 14a', 14b, 14b' and 14c, (3) after being disconnected from the network, and/or (4) from stoppage of movement (e.g., in decision step 104 of method 101). Using a random time interval for each particular secondary wireless transceiver device 14b, 14b' can minimize signal traffic (opposed to signal traffic if all secondary wireless transceiver devices 14b, 14b' in a single room all sent queries at the same time after they all received a signal). Limiting the frequency of queries can also allow for the secondary wireless transceiver devices 14b, 14b' to operate from a power source of limited current output (e.g., USB power). Furthermore, the secondary wireless transceiver device 14b, 14b' can go into sleep mode if no response is received after a particular number of queries is sent without any response to the queries or after a particular time has passed without any response to the queries.

The illustrated secondary wireless transceiver device 14b, 14b' can be provided on the cart 99, with the cart 99 including slave devices 18, 18' used in a particular surgical operation. Likewise, it is contemplated that the main wireless transceiver device 14a, 14a' can be in a group with slave devices 18, 18' used in a particular surgical operation. To minimize signal traffic, it is contemplated that the main wireless transceiver device 14a, 14a' and the secondary wireless transceiver device 14b, 14b' having slave devices 18, 18' for a first surgical procedure can communicate using a first type of signal (e.g., a first frequency or infrared) and the main wireless transceiver device 14a, 14a' and the secondary wireless transceiver device 14b, 14b' having slave devices 18, 18' for a second surgical procedure can communicate using a second type of signal (e.g., a second frequency different than the first frequency or acoustic) such that the main wireless transceiver device 14a, 14a' and the secondary wireless transceiver devices 14b, 14b' having slave devices 18, 18' for the first surgical procedure are not able to communicate with the main wireless transceiver device 14a, 14a' and the secondary wireless transceiver devices 14b, 14b' having slave devices 18, 18' for the second surgical procedure.

It is contemplated that the system 8, 8' can perform other functions. For example, multiple wireless transceiver devices 14a, 14a', 14b, 14b' and 14c can be used to triangulate a position of any particular wireless transceiver devices 14a, 14a', 14b, 14b' and 14c to find a specific location (even in a particular room) of the wireless transceiver devices 14a, 14a', 14b, 14b' and 14c and any associated control devices 20, 20', gateways 16 and/or slave devices 18, 18'.

In the illustrated example, more than one main wireless transceiver device 14a, 14a' can be located in a particular operating room 100. It is therefore contemplated that the main wireless transceiver device 14a, 14a' can act as a secondary wireless transceiver device 14b, 14b' (e.g., by sending a wireless linking information query) to determine if a network is already established in the operating room 100. If there is already an established network, the second main wireless transceiver device 14a, 14a' will act as a secondary wireless transceiver device 14b, 14b' until the network is lost. It is also contemplated that a user can manually resolve any conflicts between two or more main wireless transceiver devices 14a, 14a' located in a particular operating room 100.

The illustrated system 8, 8' allows the medical professional to control all instruments (slave devices 18, 18') in the operating room 100 while seated and without moving (e.g., at a nurse's station) such that the medical professional does not have to leave their location or work area and navigate a crowd of instruments, carts, cables and other personnel. Moreover, more than one person can have access to control of a slave device 18, 18' (e.g., by using an interface of the slave device 18, 18' along with using the interface of the slave device 18, 18' as viewed at one or more control devices 20, 20'). The system 8, 8' replaces linking tokens and other manual connecting devices in an operating room 100 that were previously needed to connect slave devices 18 to a control device 20.

As a backup to the system 8, 8', it is contemplated that a linking token can be inserted into gateways 16, devices with gateways (wireless transceiver devices, control devices or slave devices) or devices connected to the gateways 16 to provide the wireless linking information to all gateways 16 or devices with gateways. Alternatively, it is contemplated that a short-range wireless-enabled token (e.g., a token capable of communicating via infrared, acoustic or RFID signals) can be positioned by the wireless transceiver devices to provide the wireless linking information to all gateways 16 or devices with gateways.

In the embodiments outlined above, each of the slave devices 18 and the control devices 20 have an IP address on the network (or something similar) such that packets of information sent between the slave devices 18 and the control devices 20 over the gateways 16 reach their intended destination (or over any network that connects the slave devices 18 and the control devices 20 as established by the wireless transceiver devices 14a, 14b, 14a', 14b'). However, it is contemplated that the slave devices 18 and the control devices 20 could be configured to send packets of information without network addresses attached to the packets. In such a situation, the system for automatically networking devices 8 must be configured to ensure that the packets reach the proper destination.

Figure 9:
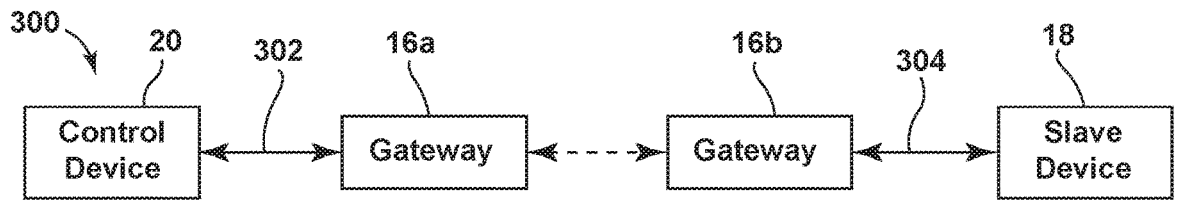
FIG. 9 illustrates a first configuration for ensuring packets of information sent between the slave devices and the control devices over the gateways reach their intended destination.

FIG. 9 illustrates a first configuration 300 for ensuring packets of information sent between the slave devices 18 and the control devices 20 over the gateways 16 reach their intended destination. FIG. 9 includes the control device 20 wired to a first gateway 16a by first wiring 302 and a slave device 18 wired to a second gateway 16b by second wiring 304.

In the illustrated example, the first gateway 16a is programmed with the address information of the second gateway 16b and the second gateway 16b is programmed with the address information of the first gateway 16a. Therefore, packets of information sent from the control device 20 to the first gateway 16a will have the address of the second gateway 16b added thereto by the first gateway 16a such that when the first gateway 16a wirelessly communicates the packets of information from the control device 20, the second gateway 16b receives the packets of information. The second gateway 16b then removes the address information from the packets of information and sends the packets of information to the slave device 18. Likewise, packets of information sent from the slave device 18 to the second gateway 16b will have the address of the first gateway 16a added thereto by the second gateway 16b such that when the second gateway 16b wirelessly communicates the packets of information from the slave device 18, the first gateway 16a receives the packets of information. The first gateway 16a then removes the address information from the packets of information and sends the packets of information to the control device 20. Accordingly, the control device 20 and the slave device 18 are able to communicate without directly themselves including destination addresses to the packets of information transmitted therefrom.

In the illustrated first configuration 300 as outlined above, the control device 20 communicates with the first gateway 16a over the first wiring 302, the slave device 18 communicates with the second gateway 16b over the second wiring 304 and the first gateway 16a and the second gateway 16b communicate with each other wirelessly. As outlined above, the first gateway 16a and the second gateway 16b can form the wireless network or the wireless network used by the first gateway 16a and the second gateway 16b could occur over a pre-established hospital network. It is contemplated that the first gateway 16a and the second gateway 16b could include a single port or a plurality of ports for connection to the first wiring 302 and the second gateway 16b, respectively. If the first gateway 16a and the second gateway 16b include a single port, the single port could be limited to a particular type of port. For example, the single port could be a port for Ethernet, FireWire, USB or a serial port according to the RS-232 standard. The single port on the first gateway 16a and the second gateway 16b could be the same type as the port on the control device 20 and the slave device 18, respectfully. Alternatively, the single port on the first gateway 16a and the second gateway 16b could be different than the type of port on the control device 20 and the slave device 18, with the first wiring 302 and the second wiring 304 having different port connectors on either end thereof (e.g., FireWire on a first end and USB on a second end). It is further contemplated that the first gateway 16a and the second gateway 16b could include a plurality of ports such that the wiring 302, 304 could have the same port connector on each end thereof and the proper port on the first gateway 16a and the second gateway 16b could be used depending on the port of the control device 20 and the slave device 18, respectively. All of the control device 20, the gateways 16a, 16b and the slave device 18 can be configured to be hot-swappable or cold-swappable.

Figure 10:
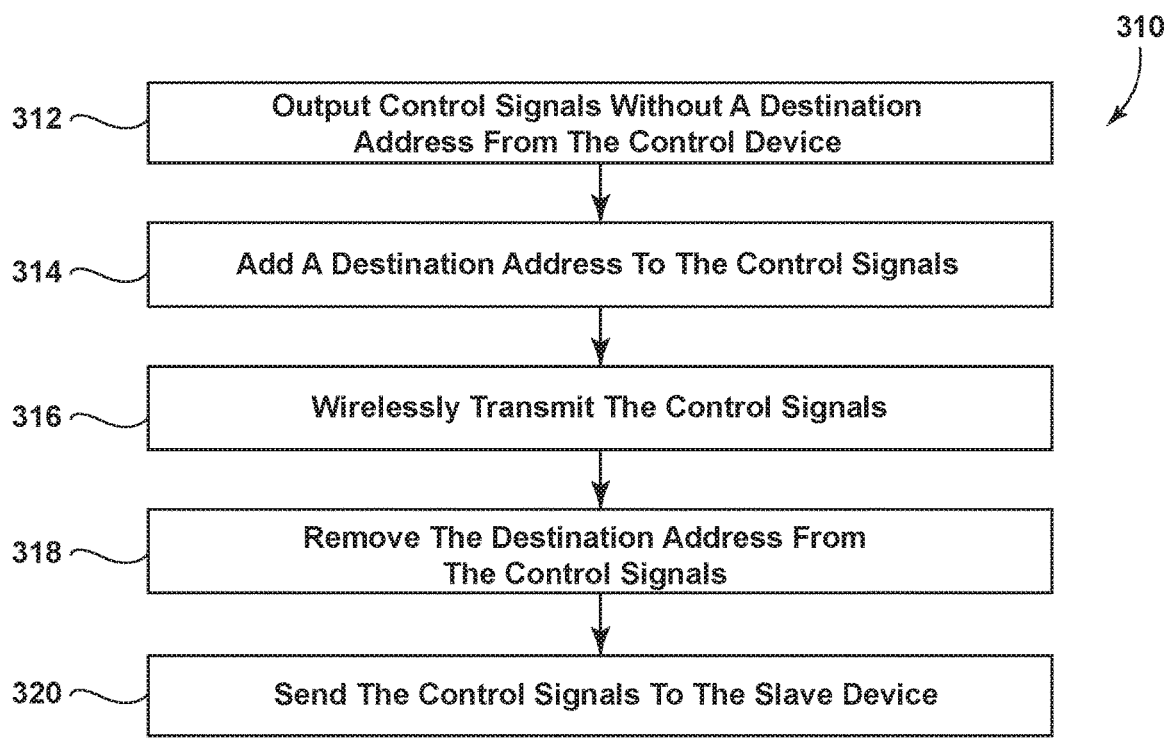
FIG. 10 illustrates a method of controlling the slave device using the first configuration of FIG. 9.

FIG. 10 illustrates a method 310 of controlling the slave device 18 using the first configuration 300 of FIG. 9. The method 310 includes outputting control signals without a destination address from the control device 20 to the first gateway 16a at step 312, adding a destination address for the second gateway 16b to the control signals with the first gateway 16a at step 314, wirelessly transmitting the control signals from the first gateway 16a to the second gateway 16b at step 316, removing the destination address for the second gateway 16b from the control signals with the second gateway 16b at step 318, and sending the control signals from the second gateway 16b to the slave device 18 at step 320. Information is sent from the slave device 18 to the control device 20 in the reverse direction using the same process as set forth in FIG. 10.

Figure 11:
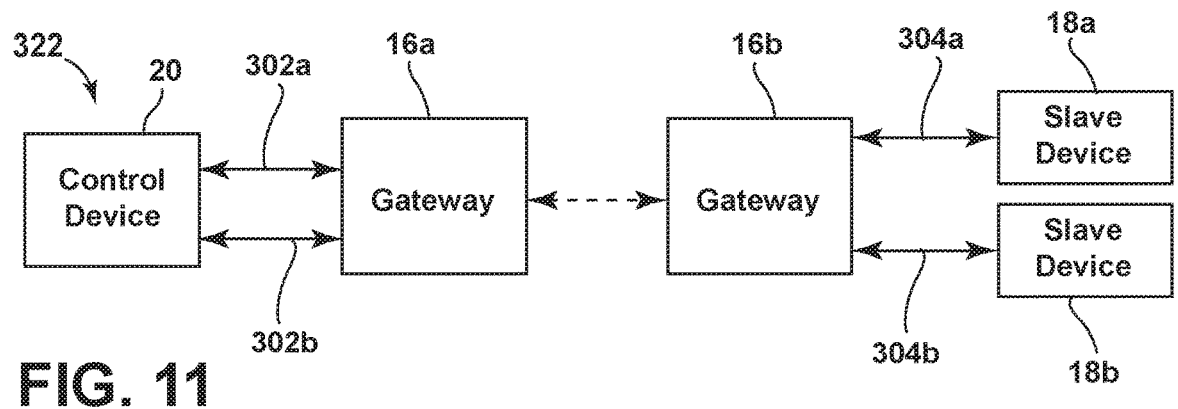
FIG. 11 illustrates a second configuration for ensuring packets of information sent between the slave devices and the control devices over the gateways reach their intended destination.

FIG. 11 illustrates a second configuration 322 for ensuring packets of information sent between the control device 20 and a plurality of the slave devices 18 over the gateways 16 reach their intended destination. FIG. 11 includes the control device 20 wired to the first gateway 16a by the first wiring 302a and by third wiring 302b. FIG. 11 also includes a first slave device 18a wired to the second gateway 16b by the second wiring 304a and a second slave device 18b wired to the second gateway 16b by fourth wiring 304b.

In the illustrated example, the first gateway 16a is programmed with the address information of the second gateway 16b and the second gateway 16b is programmed with the address information of the first gateway 16a. Moreover, the first gateway 16a is programmed with port information of the second gateway 16b (in the illustrated example, information related to the ports wherein the second wiring 304a and the fourth wiring 304b connect to the second gateway 16b, either removably or fixedly) and the second gateway 16b is programmed with port information of the first gateway 16a (in the illustrated example, information related to the ports wherein the first wiring 302a and the third wiring 302b connect to the first gateway 16a, either removably or fixedly). Therefore, packets of information sent from the control device 20 to the first gateway 16a over the first wiring 302a will have the address of the second gateway 16b added thereto along with port information related to the port of the second wiring 304a by the first gateway 16a such that when the first gateway 16a wirelessly communicates the packets of information from the control device 20 delivered by the first wiring 302a, the second gateway 16b receives the packets of information for sending on the second wiring 304a. The second gateway 16b then removes the address information along with the port information from the packets of information originally sent through the first wiring 302a and sends the packets of information to the first slave device 18a over the second wiring 304a. Likewise, packets of information sent from the control device 20 to the first gateway 16a over the third wiring 302b will have the address of the second gateway 16b added thereto along with port information related to the port of the fourth wiring 304b by the first gateway 16a such that when the first gateway 16a wirelessly communicates the packets of information from the control device 20 delivered by the third wiring 302b, the second gateway 16b receives the packets of information for sending on to the fourth wiring 304b. The second gateway 16b then removes the address information along with the port information from the packets of information originally sent through the third wiring 302b and sends the packets of information to the second slave device 18b over the fourth wiring 304b.

In a similar manner, packets of information sent from the first slave device 18a to the second gateway 16b over the second wiring 304a will have the address of the first gateway 16a added thereto along with information related to the port of the first wiring 302a by the second gateway 16b such that when the second gateway 16b wirelessly communicates the packets of information from the first slave device 18a delivered by the second wiring 304a, the first gateway 16a receives the packets of information for sending on the first wiring 302a. The first gateway 16a then removes the address information along with the port information from the packets of information originally sent through the second wiring 304a and sends the packets of information to the control device 20 over the first wiring 302a. Likewise, packets of information sent from the second slave device 18b to the second gateway 16b over the fourth wiring 304b will have the address of the first gateway 16a added thereto along with information related to the port of the third wiring 302b by the second gateway 16b such that when the second gateway 16b wirelessly communicates the packets of information from the second slave device 18b delivered by the fourth wiring 304b, the first gateway 16a receives the packets of information for sending on the third wiring 302b. The first gateway 16a then removes the address information along with the port information from the packets of information originally sent through the fourth wiring 304b and sends the packets of information to the control device 20 over the third wiring 302b. It is contemplated that any number of slave devices 18 could be connected to the second gateway 16b and that port information is transmitted between the first gateway 16a and the second gateway 16b as outlined above for each slave device 18 connected to the second gateway 16b to ensure that the packets of information reach their intended destination.

In the illustrated example, the first gateway 16a and the second gateway 16b can form the wireless network or the wireless network used by the first gateway 16a and the second gateway 16b could occur over a pre-established hospital network. Furthermore, the first gateway 16a and the second gateway 16b could include any type of ports connected to the first wiring 302a, the second wiring 304a, the third wiring 302b and the fourth wiring 304b (either matching the ports on the control device 20 or the slave devices 18a, 18b or being different as outlined above in the first configuration 300). All of the control device 20, the gateways 16a, 16b and the slave devices 18a, 18b can be configured to be hot-swappable or cold-swappable.

Figure 12:
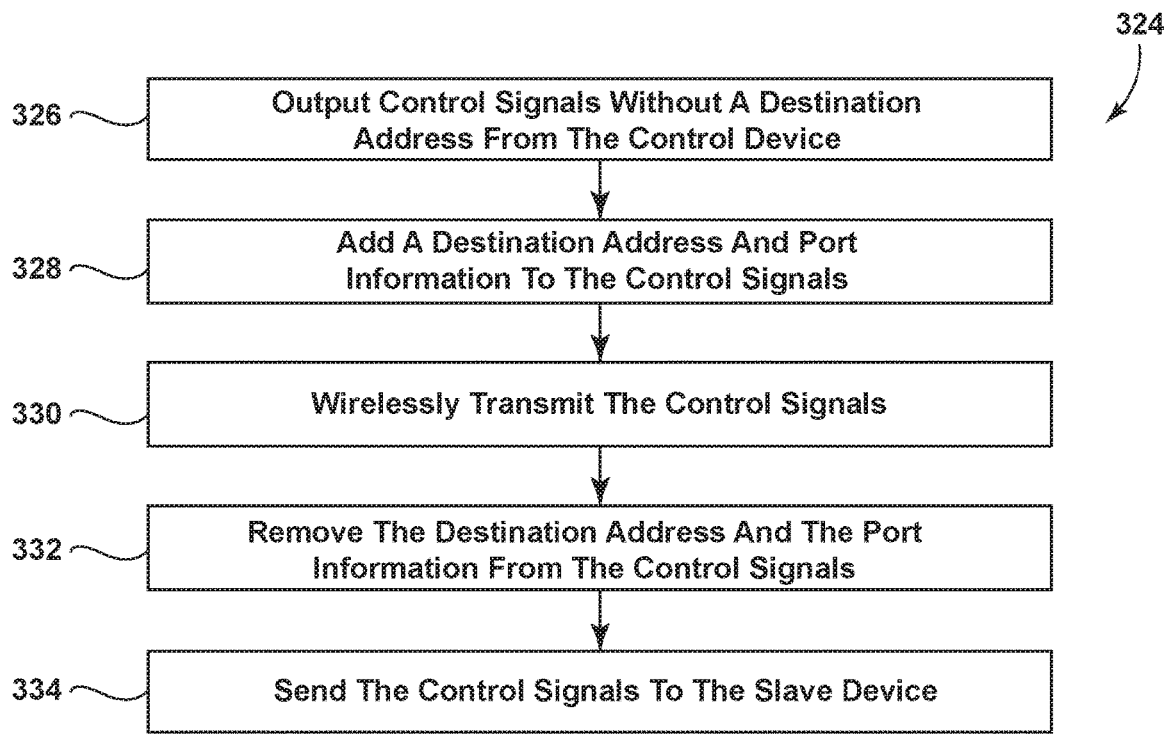
FIG. 12 illustrates a method of controlling the slave device using the second configuration of FIG. 11.

FIG. 12 illustrates a method 324 of controlling a plurality of slave devices 18 using the second configuration 322 of FIG. 11. The method 324 includes outputting control signals without a destination address from the control device 20 to the first gateway 16a at step 326, adding a destination address and port information for the second gateway 16b to the control signals with the first gateway 16a at step 328, wirelessly transmitting the control signals from the first gateway 16a to the second gateway 16b at step 330, removing the destination address and port information for the second gateway 16b from the control signals with the second gateway 16b at step 332, and sending the control signals from the second gateway 16b to the slave devices 18a, 18b at step 334. Information is sent from the slave devices 18a, 18b to the control device 20 in the reverse direction using the same process as set forth in FIG. 12.

Figure 13:
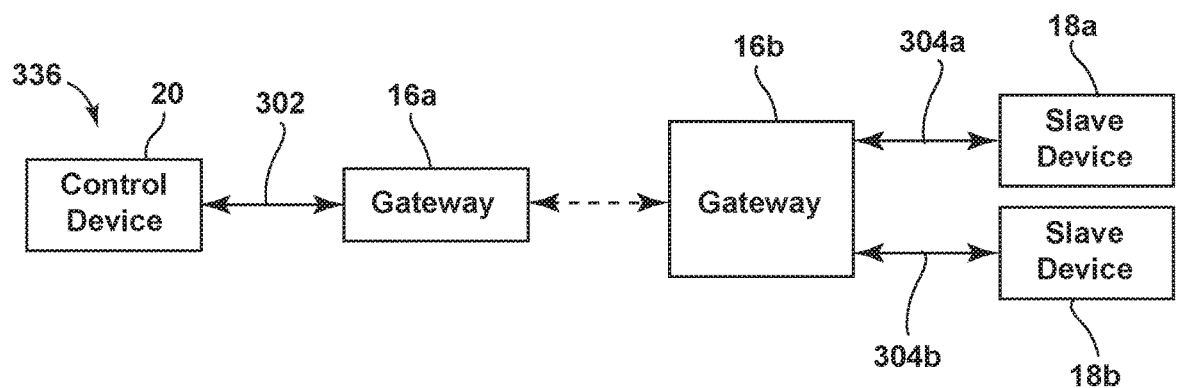
FIG. 13 illustrates a third configuration for ensuring packets of information sent between the slave devices and the control devices over the gateways reach their intended destination.

FIG. 13 illustrates a third configuration 336 for ensuring packets of information sent between the control device 20 and a plurality of the slave devices 18a, 18b over the gateways 16a, 16b reach their intended destination. The third configuration 336 is identical and functions the same as the second configuration 322 except that the control device 20 is connected to the first gateway 16a by a single wire, the first wiring 302, instead of multiple wirings. The first wiring 302 is capable of sending multiple control signals for multiple slave devices 18a, 18b, etc. For example, the first wiring 302 can be an Ethernet cable. While only two slave devices 18a, 18b are illustrated in FIG. 13, any number of slave device 18a, 18b, etc. can be connected to the second gateway 16b.

In the illustrated third configuration 336, the control device 20 and the slave devices 18a, 18b, etc. can communicate in any manner and initiation of communications can happen in any manner to ensure that the control device 20 is properly issuing command signals to the proper slave device 18a, 18b, etc. For example, the second gateway 16b can periodically send device discovery messages on the ports thereof. When the slave devices 18a, 18b, etc. are connected to the second gateway 16b, the second gateway 16b discovers the connection because the slave devices 18a, 18b etc. respond to the device discovery message. The second gateway 16b can then send a signal to the first gateway 16a reporting of the connection of the slave device 18a, 18b, etc.

along with information related to the port of the second gateway 16b to which the newly connected slave device 18a, 18b, etc. is connected. Therefore, the control device 20 can add the port information to the control signals sent therefrom to ensure that the control device 20 is properly issuing command signals to the proper slave device 18a, 18b, etc. It is also contemplated that the first gateway 16a and/or the second gateway 16b can add the port information to ensure that the control device 20 is properly issuing command signals to the proper slave device 18a, 18b, etc. without sending the port information to the control device 20.

Figure 14:
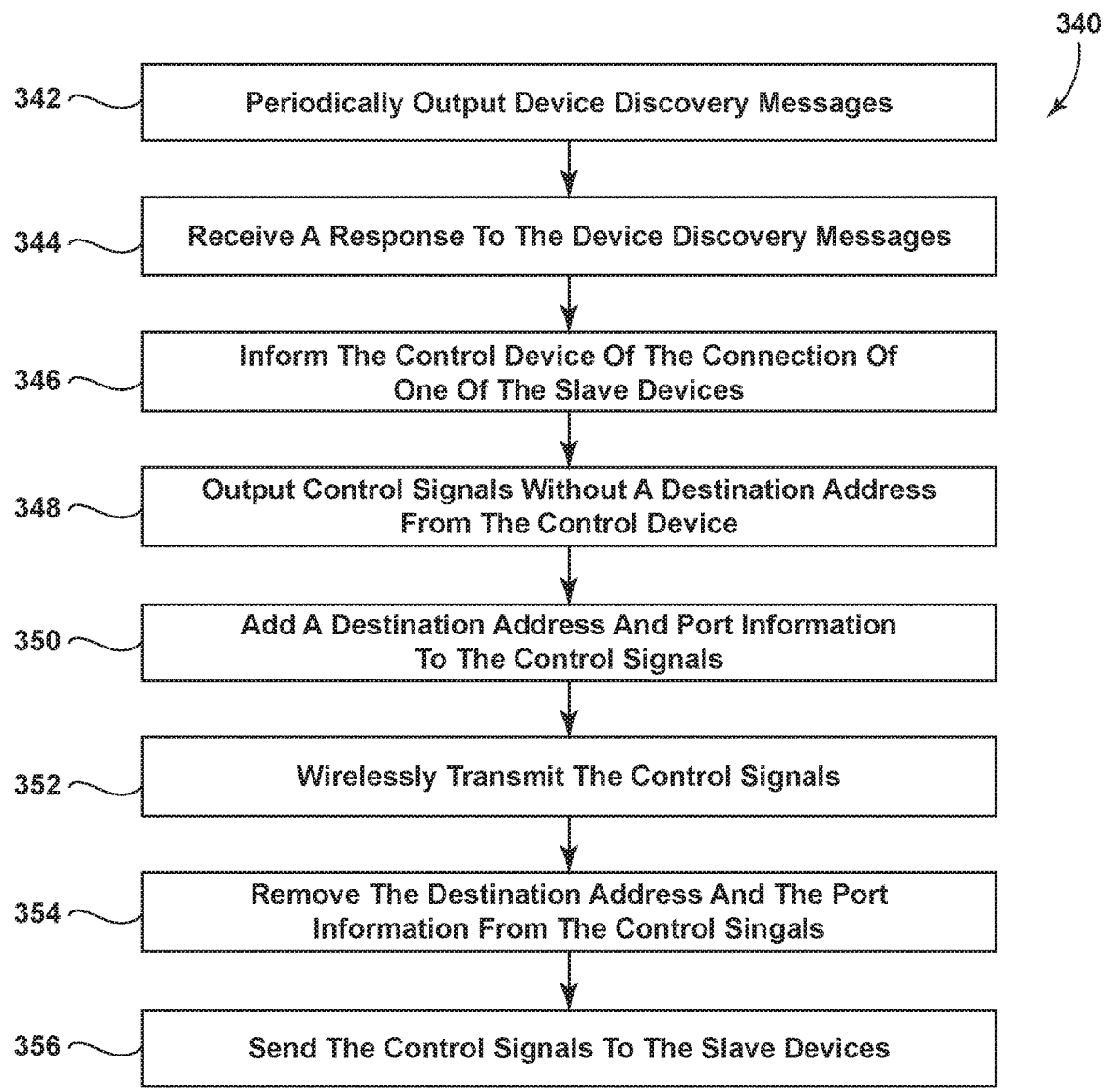
FIG. 14 illustrates a method of controlling the slave device using the third configuration of FIG. 13.

FIG. 14 illustrates a method 340 of controlling a plurality of slave devices 18 using the third configuration 336 of FIG. 13. The method 340 includes periodically outputting device discovery messages from the second gateway 16b at step 342, receiving a response to the device discovery messages from the slave devices 18a, 18b, etc. at step 344, informing the control device 20 of the connection of one of the slave devices 18a, 18b, etc. at step 346, outputting control signals without a destination address from the control device 20 to the first gateway 16a at step 348, adding a destination address and port information for the second gateway 16b to the control signals with the first gateway 16a at step 350, wirelessly transmitting the control signals from the first gateway 16a to the second gateway 16b at step 352, removing the destination address and port information for the second gateway 16b from the control signals with the second gateway 16b at step 354, and sending the control signals from the second gateway 16b to the slave devices 18a, 18b at step 356. Information is sent from the slave devices 18a, 18b, etc. to the control device 20 in the reverse direction using the same process as set forth in FIG. 14 except that steps 342, 344 and 346 are not needed once the slave devices 18a, 18b, etc. are discovered.

Figure 15:
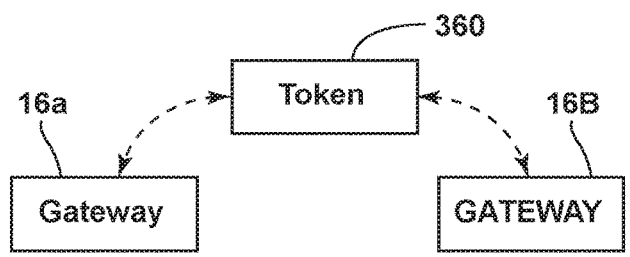
FIG. 15 illustrates a system for using a token to connect gateways of the present invention.

In all of the embodiments of FIGS. 9, 11 and 13 as outlined above, the first gateway 16a and the second gateway 16b have the address of the other gateway programmed therein to allow the first gateway 16a and the second gateway 16b to communicate. The addresses of other gateways can be programmed during manufacture of the gateways and the gateways can be sold in pairs. However, it is contemplated that the gateways can be programmed during use with the addresses of other gateways. FIG. 15 illustrates a first example of a system used to connect the first gateway 16a and the second gateway 16b. In FIG. 15, a token 360 having address information (e.g., SSID) thereon is engaged with each of the first gateway 16a and the second gateway 16b to connect the first gateway 16a and the second gateway 16b. The token 360 could be a USB flash drive insertable into each of the first gateway 16a and the second gateway 16b, an RFID chip that can be read by an RFID reader in each of the first gateway 16a and the second gateway 16b, an infrared remote that can send the address information to the first gateway 16a and the second gateway 16b or any other device that is capable of sending or providing address information to ensure that all of the devices begin operation on the same channel of a wireless link signal. By using the token 360, the first gateway 16a and the second gateway 16b can be used in combination with any other gateways. For example, the first gateway 16a can be located in a room and second gateways 16b of any secondary device group 12a, 12b, 12a', 12b' can be brought into the room and wirelessly connected to the first gateway 16a to allow the control device 20 to control the slave devices 18a, 18b, etc.

Figure 16:
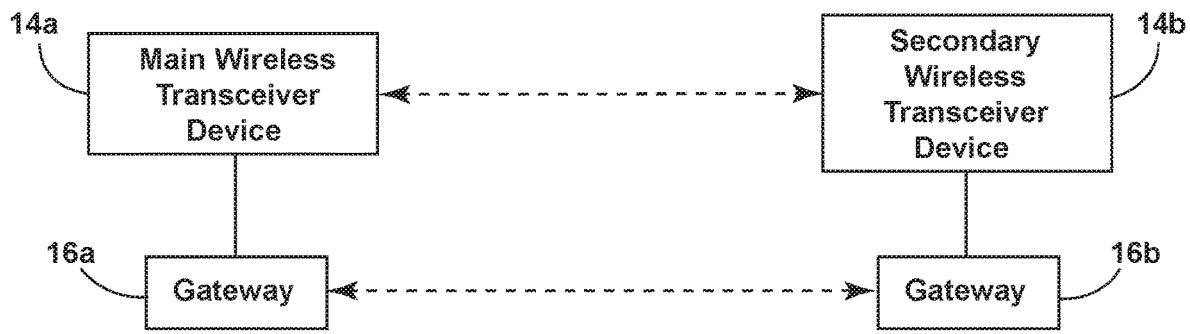
FIG. 16 illustrates a system for using wireless transceiver devices of the present invention to connect gateways of the present invention.

FIG. 16 illustrates a second example of a system used to selectively connect the first gateway 16a and the second gateway 16b. In FIG. 16, the main wireless transceiver device 14a communicates with the secondary wireless transceiver device 14b as outlined above. The main wireless transceiver device 14a sends an SSID (or other wireless network identification) and an IP address of the control device 20 (or other device identification address) to the secondary wireless transceiver device 14b. It is contemplated that the network address sent to the secondary wireless transceiver device 14b could include the address of the control device 20. The main wireless transceiver device 14a obtains the SSID (or other wireless network identification) from the first gateway 16a or provides the SSID (or other wireless network identification) to the first gateway 16a. The SSID (or other wireless network identification) sent from the main wireless transceiver device 14a to the secondary wireless transceiver device 14b is thereafter also provided to the second gateway 16b to connect the first gateway 16a and the second gateway 16b (or multiple second gateways 16b) over a wireless network (e.g., WiFi or Bluetooth™). The IP address of the control device 20 (or other device identification address) sent to the secondary wireless transceiver device 14b is sent to the second gateway 16b to allow for a connection (e.g., using a socket connection between the control device 20 and the second gateway 16b) between the slave device 18 and the control device 20 to allow the control device 20 to control the slave device 18. Alternatively, the address of the control device 20 could be included as part of the network address.

Figure 17:
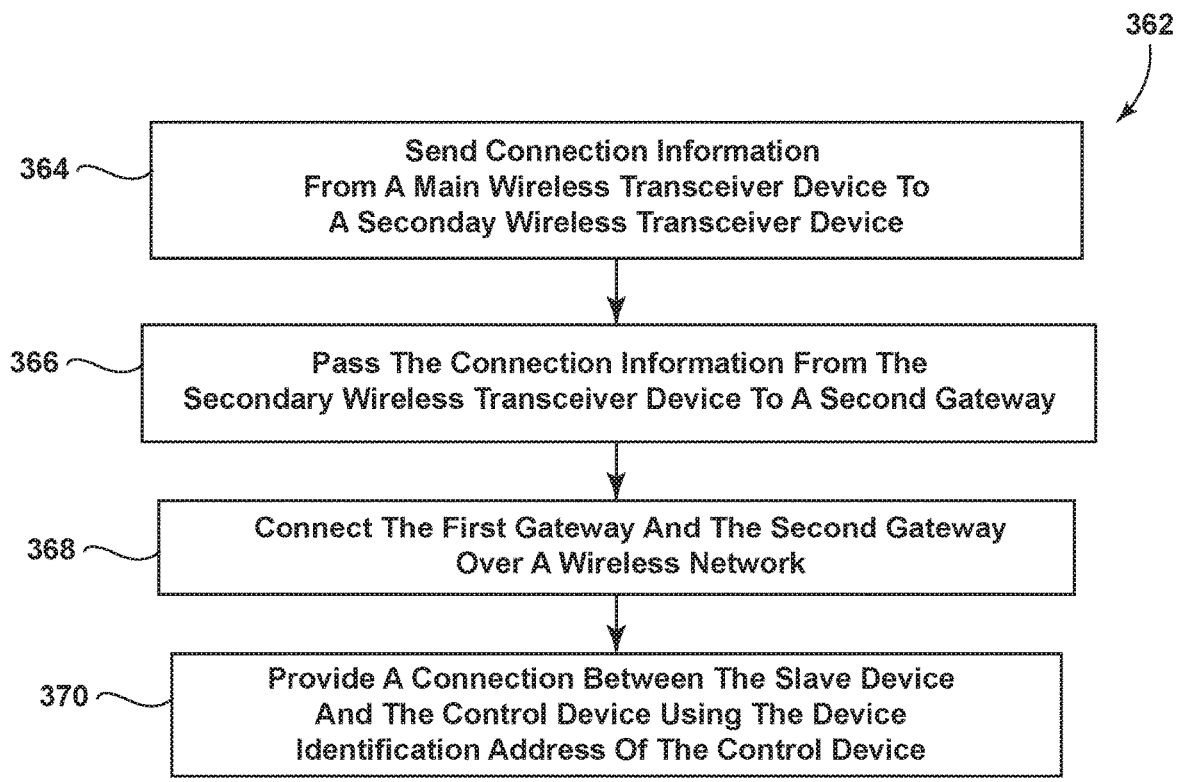
FIG. 17 illustrates a method of controlling a plurality of slave devices using the system of FIG. 16.

FIG. 17 illustrates a method 362 of controlling a plurality of slave devices 18 using the system of FIG. 16. The method 362 includes the sending of connection information (which can include a wireless network identification address that includes a device identification address of the control device 20 or a wireless network identification address that includes a device identification address of the control device 20) from the main wireless transceiver device 14a to the secondary wireless transceiver device 14b at step 364, passing the connection information from the secondary wireless transceiver device 14b to the second gateway 16b at step 366, connecting the first gateway 16a and the second gateway 16b over a wireless network at step 368, and providing a connection between the slave device 18 and the control device 20 using the device identification address of the control device 20 at step 370. The method 362 can use the method 340 of controlling a plurality of slave devices 18 using the third configuration 336 of FIG. 13 as outlined above to connect a plurality of slave devices 18 to the control device 20. The method 362 can also use other manners of discovering slave devices 18 as outlined below.

The systems and embodiments of FIGS. 9, 11, 13, 15 and 16 illustrate methods of wirelessly connecting the first gateway 16a to a single second gateway 16b. However, all of the systems and embodiments of FIGS. 9, 11, 13, 15 and 16 can be used to connect the first gateway 16a to a plurality of second gateways 16b. For the embodiments of FIGS. 9, 11 and 13, the first gateway 16a and a plurality of second gateways 16b can be programmed to communicate with each other. For the embodiment of FIG. 15, the token 360 can be used to link the first gateway 16a and a plurality of the second gateways 16b. For the embodiment of FIG. 16, the main wireless transceiver device 14a can communicate with a plurality of secondary wireless transceiver devices 14b as outlined above to link the first gateway 16a with a plurality of the second gateways 16b. It is contemplated that the first gateway 16a and the second gateway 16b or a plurality of second gateways 16b could be connected in other manners (e.g., using a location service and wirelessly sending the location of the first gateway 16a and the second gateway 16b thereto (for example, over a building wide WiFi network)). Moreover, it is contemplated that the control device 20 can be wired to slave devices 18 through the first gateway 16a. Therefore, the control device 20 can control all devices in a room including those on the same cart or shelf via wires to the first gateway 16a and to the slave devices 18 and wirelessly to other slave devices 18. For the embodiments of FIGS. 15 and 16, the first gateway 16a and the second gateway 16b (or plurality of second gateways 16b) can terminate the network and/or connection(s) when the control device 20 is powered down, when the slave device 18 is powered down, when the first gateway 16a is powered down, when the second gateway 16b is powered down and/or when the network is down. It is further contemplated that the network and/or connection(s) can be selectively and manually disconnected.

In communications between the control device 20 and the slave devices 18, the slave devices 18 must be able to understand and implement the packets of information sent to the slave devices 18 from the control device 20. Likewise, the control device 20 must be able to understand packets of information sent thereto from the slave devices 18. Therefore, the control device 20 must send packets of information to the slave devices 18 using a serial port operating mode or protocol (e.g., at a specific baud) that the slave devices 18 can understand. An aspect of the present invention is to provide a system to ensure that the control device 20 issues commands to the slave devices 18 using a serial port operating mode or protocol that the slave devices 18 can understand.

Figure 18:
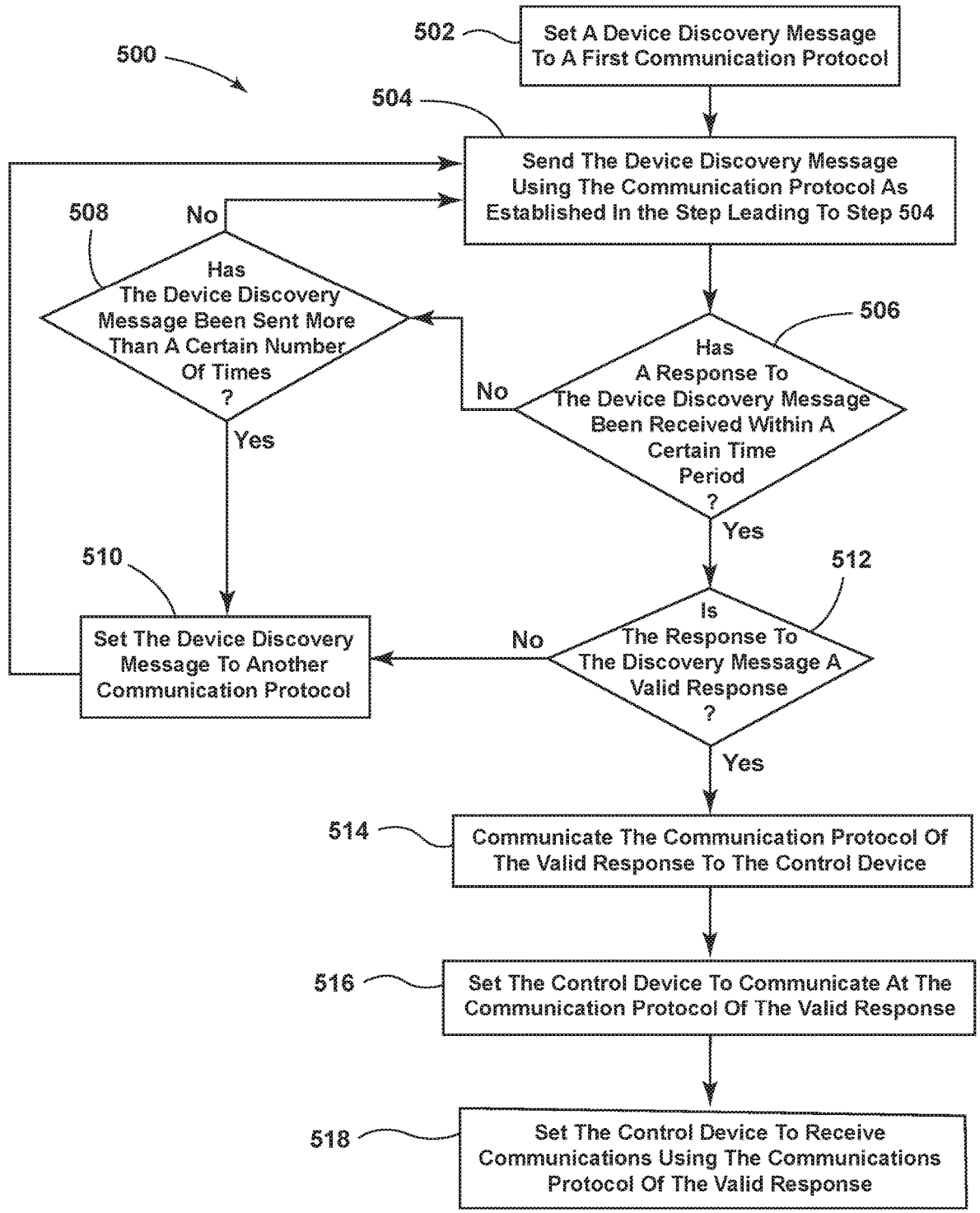
FIG. 18 illustrates a method of establishing a communication protocol between the slave device and the control device of the present invention.

In the illustrated example, the second gateway 16b connected to the slave devices 18 determines the communication protocol of the slave devices 18 to ensure that the slave devices 18 can implement the control commands in the packets of information sent thereto from the control device 20. FIG. 18 illustrates a method 500 of establishing a communication protocol between the slave device 18 and the control device 20. At step 502, the method 500 is initiated and a device discovery message is set to a first communication protocol (e.g., at 9600 bps). At step 504, the second gateway 16b sends the device discovery message on a serial port thereof to which the slave device 18 is connected at step 504, with the device discovery message using the communication protocol as established in the step leading to step 504 (initially the first communication protocol as established at step 502).

In the illustrated example, if the second gateway 16b does not receive a response to the device discovery message at step 504 within a certain time period at decision step 506, the method 500 proceeds to decision step 508. At decision step 508, the method 500 determines if the device discovery message using the communication protocol as established in the step leading to step 504 (initially the first communication protocol as established at step 502) has happened more than a certain number of times. If the device discovery message using the communication protocol as established in the step leading to step 504 (initially the first communication protocol as established at step 502) has happened less than a certain number of times as determined at step 508, the method 500 proceeds back to step 504 to resend the device discovery message using the communication protocol as established in the step leading to step 504 (initially the first communication protocol as established at step 502).

If the device discovery message using the communication protocol as established in the step leading to step 504 (initially the first communication protocol as established at step 502) has happened the certain number of times as determined at step 508, the method 500 proceeds to step 510 wherein the device discovery message is set to another communication protocol (e.g., at 19200 bps). After step 510, the method 500 proceeds back to step 504 wherein the device discovery message is sent using the communication protocol as established in step 510 (i.e., using another communication protocol). The method 500 then proceeds to step 506 and step 508, if appropriate. If the device discovery message using the communication protocol as established in the step leading to step 504 (another communication protocol as established at step 510) has happened the certain number of times as determined at step 508, the method 500 proceeds back to step 510 wherein the device discovery message is set to yet another communication protocol (e.g., back to 9600 bps or another communication protocol). Once initiated, the method 500 continues in a loop of steps 504, 506, 508 and 510 until the second gateway 16b receives a response to the device discovery message sent at step 504 within the certain time period at decision step 506, at which point the method 500 proceeds to decision step 512.

In the illustrated example, the method 500 determines if the response to the device discovery message is a valid response at decision step 512. If the response to the device discovery message is a not a valid response as determined at step 512, the method 500 proceeds to step 510 as outlined above wherein the communication protocol of the device discovery message is altered. However, if the response to the device discovery message is a valid response as determined at step 512, the method 500 proceeds to step 514 wherein the communication protocol of the valid response as sent at step 504 (and established at step 502 or 510) is communicated to the control device 20. The control device 20 is then set to communicate at the communication protocol of the valid response as sent at step 504 at step 516. Moreover, the control device 20 is set to receive communications using the communication protocol of the valid response as sent at step 504 at step 518.

The illustrated method 500 of establishing a communication protocol between the slave device 18 and the control device 20 includes sending the device discovery message with the second gateway 16b at step 504. Since the method 500 does not send a wireless communication until step 514, the method 500 can minimize wireless communications. However, it is contemplated that the device discovery message sent at step 504 could be sent from the first gateway 16a wirelessly to the second gateway 16b at step 504 (with a response to the device discovery message being wirelessly sent back to the first gateway 16a) or from the control device 20 to the second gateway 16b via the first gateway 16a. It is further contemplated that the method 500 can omit step 508 and have step 506 directly proceed to step 510 if a replay to the device discovery message it not received in the certain time period.

Figure 19:
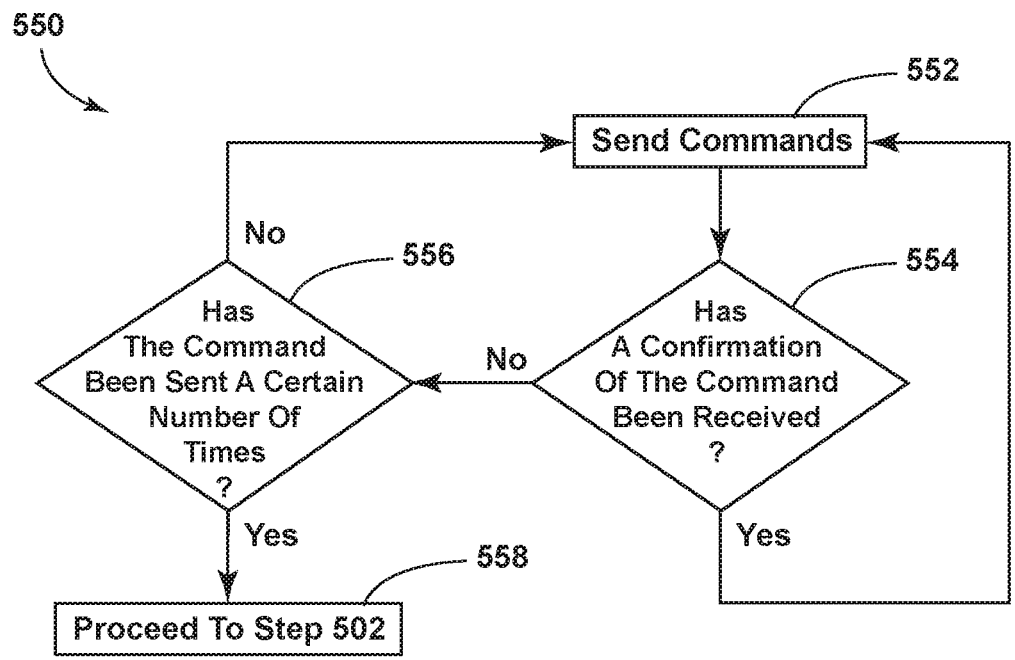
FIG. 19 illustrates a method of sending commands using the communication protocol as set in the method of FIG. 18.

FIG. 19 illustrates a method 550 of sending commands using the communication protocol as set by step 516 and 518 of the method 500 establishing a communication protocol between the slave device 18 and the control device 20. First, at step 552, the control device 20 sends commands to the slave device 18. At decision step 554, a determination is made if a confirmation of the command is received by the control device 20 within a certain time period. If the confirmation of the command is received by the control device 20 within the certain time period as determined by step 554, the method returns to step 552 wherein further commands can be sent from the control device 20 to the slave device 18. If the confirmation of the command is not received by the control device 20 within the certain time period as determined by step 554, the method proceeds to decision step 556 wherein there is a determination if the command of step 552 has been sent a certain number of times. If the command of step 552 has not been sent the certain number of times as determined at step 556, the method 550 proceeds back to step 552 wherein the command is sent again. If the command of step 552 has been sent the certain number of times as determined at step 556, the method 550 proceeds to step 502 of method 500 at step 558 along with resetting the control device 20 to no longer communicate at the communication protocol of the valid response as set by step 516 and no longer be set to receive communications using the communication protocol as set by step 518.

Some control devices 20 (and communication protocols used by the control devices 20) are configured to continuously send status update requests to the slave devices 18 connected thereto (e.g., every 250 ms). The response to the status update requests can be a notification that the status of the slave device 18 has not changed. If no status update is received, the control device 20 then knows that the slave device 18 has been disconnected (or powered down). However, continuously sending status update requests can substantially increase wireless traffic using the first gateway 16a and the second gateway 16b as outlined above. Therefore, the first gateway 16a can be configured to ignore or not forward status update requests received from the control device 20. Furthermore, the second gateway 16b can be configured to send the status update requests to the slave devices 18 connected thereto according to the method 600 of requesting updates of FIG. 19.

Figure 20:
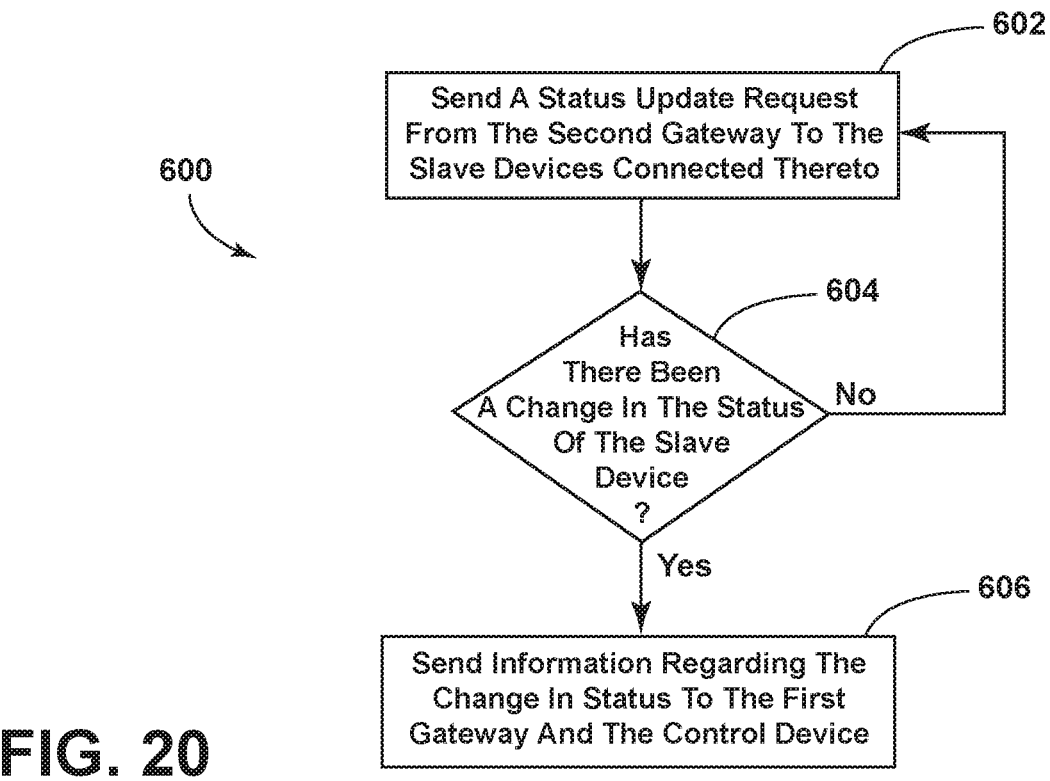
FIG. 20 illustrates a method of reducing wireless traffic using the gateways of the present invention.

In the illustrated example, the method 600 of requesting updates of FIG. 20 includes sending a status update request from the second gateway 16b to the slave devices 18 connected thereto at step 602. If there is no change in the status of the slave device 18 as determined at decision step 604, the method 600 returns to step 602. However, if there is a change in the status of the slave device 18 as determined at decision step 604 (e.g., the slave device 18 is disconnected or a parameter of the slave device 18 changes through internal events or through user interaction), the method 600 proceeds to step 606 wherein the information regarding the change in status is sent to the first gateway 16a and the control device 20 at step 606. Therefore, the method 600 of requesting updates of FIG. 19 reduces wireless traffic.

Although particular preferred embodiments of the invention have been disclosed in detail for illustrative purposes, it will be recognized that variations or modifications of the disclosed apparatus, including the rearrangement of parts, lie within the scope of the present invention. For example, the control device 20 and the slave devices 18 of FIGS. 9-20 can be any of the control devices 20 or slave devices 18 as disclosed herein. Furthermore, all of the wiring 302, 302a, 302b, 304, 304a and 304b can be any type of wiring (e.g., Ethernet) and can be removably or permanently connected to the control devices 20, the slave devices 18 and the gateways 16a, 16b. Moreover, it is contemplated that the main wireless transceiver devices 14a, 14a' can be integrated with the control devices 20, 20' and/or the slave devices 18, 18'. Likewise, it is contemplated that the secondary wireless transceiver devices 14b, 14b' can be integrated with the slave devices 18, 18'. Moreover, it is contemplated that any device that controls another device is a control device and any device that can be controlled is a slave device and that a single device can be both a slave device when it is being controlled and a control device when it controls another device. It is contemplated that the control device and the gateway device could be in a single housing and that the slave device and the gateway device could be in a single housing. It is further contemplated that any of the control device, gateway device and/or wireless transceiver device could be in a single housing and that any of the slave device, gateway device and/or wireless transceiver device could be in a single housing.

What is claimed is:

1. A system for automatically establishing a network comprising:
   a main device group including a main wireless transceiver device, a control device and a first network interface; and
   a secondary device group including a secondary wireless transceiver device, a secondary device group slave device and a second network interface;
   the main wireless transceiver device and the secondary wireless transceiver device being configured to wirelessly exchange networking information for networking the first network interface and the second network interface, the networking information being wirelessly exchanged via direct wireless communication between the main wireless transceiver device and the secondary wireless transceiver device,
   the main device group and the secondary device group being configured to use the networking information exchanged between the main wireless transceiver device and the secondary wireless transceiver device to form a network in which the control device communicates with the secondary device group slave device via the first network interface and the second network interface, wherein the network does not include the main wireless transceiver device and the secondary wireless transceiver device such that communication between the control device and the secondary device group slave device does not pass through the main wireless transceiver device and the secondary wireless transceiver device,
   wherein the control device wirelessly controls functions of the secondary device group slave device with instructions sent over the network.

2. The system of claim 1, wherein:
   no communication wiring extends between the main device group and the secondary device group.

3. The system of claim 1, wherein:
   the main wireless transceiver device and the secondary wireless transceiver device do not communicate with each other over the network.

4. The system of claim 1, wherein:
   the control device and the first network interface are located in a single housing.

5. The system of claim 1, wherein:
   at least one of the main device group and the secondary device group are located on a portable cart.

6. The system of claim 1, wherein:
   the main device group further includes a main device group slave device, the control device controlling functions of the main device group slave device.

7. The system of claim 6, wherein:
   the control device and the main device group slave device are located in a single housing.

8. The system of claim 1, wherein:
   the secondary device group slave device and the second network interface are located in a single housing.

9. The system of claim 1, wherein:
the main wireless transceiver device includes a main motion sensor for sensing motion of the main wireless transceiver device.

10. The system of claim 9, wherein:
the secondary wireless transceiver device includes a secondary motion sensor for sensing motion of the secondary wireless transceiver device.

11. The system of claim 10, wherein:
the main wireless transceiver device sends a wakeup broadcast when the main motion sensor senses stoppage of motion of the main wireless transceiver device.

12. The system of claim 11, wherein:
the secondary wireless transceiver device sends a request for wireless linking information when the secondary motion sensor senses stoppage of motion of the secondary wireless transceiver device.

13. The system of claim 1, wherein:
the main wireless transceiver device sends a wakeup broadcast on powering of the main wireless transceiver device.

14. The system of claim 1, wherein:
the secondary wireless transceiver device sends a request for wireless linking information when the secondary motion sensor senses stoppage of motion of the secondary wireless transceiver device.

15. The system of claim 1, wherein:
the secondary wireless transceiver device includes a secondary motion sensor for sensing motion of the secondary wireless transceiver device.

16. The system of claim 1, further including:
a room wireless transceiver device fixed in the single location, the room wireless transceiver device broadcasting a room ID.

17. The system of claim 1, wherein:
the main wireless transceiver device and the secondary wireless transceiver device each wirelessly communicate using at least one of infrared, acoustic and radio waves, with at least one of the at least one of the infrared, acoustic and radio waves not being able to pass through the walls of the single location.

18. The system of claim 1, wherein:
wireless communications of the main wireless transceiver device and the secondary wireless transceiver device are not able to pass through walls of the single location.

19. A method for controlling a device comprising:
providing a main device group including a main wireless transceiver device, a control device and a first network interface;
providing a secondary device group including a secondary wireless transceiver device, a slave device and a second network interface;
wirelessly exchanging networking information for networking the first network interface and the second network interface via direct wireless communication between the main wireless transceiver device and the secondary wireless transceiver device;
forming a network over the first network interface and the second network interface using the networking information exchanged between the main wireless transceiver device and the secondary wireless transceiver device, wherein the network does not include the main wireless transceiver device and the secondary wireless transceiver device such that communication between the control device and the secondary device group slave device does not pass through the main wireless transceiver device and the secondary wireless transceiver device; and
controlling functions of the slave device with the control device through instructions sent over the network.

20. The method of claim 19, wherein:
no communication wiring extends between the main device group and the secondary device group.

21. The method of claim 19, wherein:
the main wireless transceiver device and the secondary wireless transceiver device do not communicate with each other over the network.

22. The method of claim 19, further including:
locating the control device and the first network interface in a single housing.

23. The method of claim 19, further including:
positioning at least one of the main device group and the secondary device group on a portable cart.

24. The method of claim 19, further including:
providing the main device group with a main device group slave device; and
controlling functions of the main device group slave device with the control device.

25. The method of claim 24, further including:
locating the control device and the main device group slave device in a single housing.

26. The method of claim 19, further including:
locating the slave device and the second network interface in a single housing.

27. The method of claim 19, wherein:
wherein the step of wirelessly communicating comprising sending at least one of infrared, acoustic and radio waves that are not able to pass through the walls of the single location.

28. The method of claim 19, further including:
broadcasting a request for the network information, the request for the network information being broadcast by the secondary wireless transceiver device.

29. The method of claim 19, further including:
broadcasting a wakeup signal, the wakeup signal being broadcast by the main wireless transceiver device.

30. The method of claim 29, further including:
broadcasting a request for the network information, the request for the network information being broadcast by the secondary wireless transceiver device after the step of broadcasting the wakeup signal.

31. The method of claim 19, further including:
providing the main wireless transceiver device with a main motion sensor for sensing movement of the main wireless transceiver device.

32. The method of claim 31, further including:
moving the main device group; and
sensing movement of the main wireless transceiver device with the main motion sensor.

33. The method of claim 32, further including:
stopping motion of the main device group;
broadcasting a wakeup signal when the main motion sensor senses that the main device group has stopped moving, the wakeup signal being broadcast by the main wireless transceiver device.

34. The method of claim 33, further including:
broadcasting a request for the network information, the request for the network information being broadcast by the secondary wireless transceiver device after the step of broadcasting the wakeup signal.

35. The method of claim 32, further including:
broadcasting a refresh signal when the main motion sensor senses that the main device group has begun moving, the refresh signal being broadcast by the main wireless transceiver device; and
broadcasting a request for the network information, the request for the network information being broadcast by the secondary wireless transceiver device after the step of broadcasting the refresh signal.

36. The method of claim 19, further including:
providing the secondary wireless transceiver device with a secondary motion sensor for sensing movement of the secondary wireless transceiver device.

37. The method of claim 36, further including:
moving the secondary device group; and
sensing movement of the secondary wireless transceiver device with the secondary motion sensor.

38. The method of claim 37, further including:
stopping motion of the secondary device group;
broadcasting a request for the network information when the secondary motion sensor senses that the main device group has stopped moving.

39. The method of claim 19, further including:
providing a room wireless transceiver device at the single location; and
broadcasting a room ID with the room wireless transceiver device.

40. The method of claim 39, further including:
broadcasting a room ID query from the main wireless transceiver device.

41. The method of claim 39, further including:
broadcasting a room ID query from the secondary wireless transceiver device.

42. The method of claim 19, wherein:
wireless communications of the main wireless transceiver device and the secondary wireless transceiver device are not able to pass through walls of the single location.

43. A system for automatically establishing a network comprising:
a main device group including a main wireless transceiver device, a first device and a first network interface, wherein the main transceiver device, the first device, and the first network interface are communicatively wired together; and
a secondary device group including a secondary wireless transceiver device, a secondary device and a second network interface, wherein the secondary transceiver device, the secondary device, and the second network interface are communicatively wired together;
the main wireless transceiver device and the secondary wireless transceiver device being configured to wirelessly exchange networking information for networking the first network interface and the second network interface, the networking information being wirelessly exchanged via direct wireless communication between the main wireless transceiver device and the secondary wireless transceiver device,
the main device group and the secondary device group being configured to use the networking information exchanged between the main wireless transceiver device and the secondary wireless transceiver device to form a network wherein the first device communicates with the secondary device over the first network interface and the second network interface, wherein the network does not include the main wireless transceiver device and the secondary wireless transceiver device such that communication between the first device and the secondary device does not pass through the main wireless transceiver device and the secondary wireless transceiver device.

* * * * *